US011325939B2

(12) United States Patent
Guo et al.

(10) Patent No.: US 11,325,939 B2
(45) Date of Patent: *May 10, 2022

(54) RNA NANOPARTICLES FOR BRAIN TUMOR TREATMENT

(71) Applicant: University of Kentucky Research Foundation, Lexington, KY (US)

(72) Inventors: Peixuan Guo, Columbus, OH (US); Carlo M. Croce, Columbus, OH (US); Tae Jin Lee, Columbus, OH (US); Farzin Haque, Long Island City, NY (US); Hui Li, Columbus, OH (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/813,087

(22) Filed: Mar. 9, 2020

(65) Prior Publication Data

US 2021/0115083 A1   Apr. 22, 2021

Related U.S. Application Data

(62) Division of application No. 15/554,360, filed as application No. PCT/US2016/021447 on Mar. 9, 2016, now Pat. No. 10,584,144.

(60) Provisional application No. 62/130,459, filed on Mar. 9, 2015.

(51) Int. Cl.
```
C07H 21/04      (2006.01)
C07H 21/02      (2006.01)
C12N 15/113     (2010.01)
A61K 47/55      (2017.01)
C12N 15/11      (2006.01)
A61K 47/69      (2017.01)
A61P 35/00      (2006.01)
C12N 15/115     (2010.01)
B82Y 5/00       (2011.01)
```
(52) U.S. Cl.
CPC ........... *C07H 21/02* (2013.01); *A61K 47/551* (2017.08); *A61K 47/6929* (2017.08); *A61P 35/00* (2018.01); *C12N 15/111* (2013.01); *C12N 15/113* (2013.01); *C12N 15/115* (2013.01); *B82Y 5/00* (2013.01); *C12N 2310/113* (2013.01); *C12N 2310/14* (2013.01); *C12N 2310/3231* (2013.01); *C12N 2310/52* (2013.01); *C12N 2320/32* (2013.01)

(58) Field of Classification Search
None
See application file for complete search history.

(56) References Cited

U.S. PATENT DOCUMENTS

| | | |
|---|---|---|
| 6,180,082 B1 | 1/2001 | Woltering et al. |
| 6,506,559 B1 | 1/2003 | Fire et al. |
| 7,829,693 B2 | 11/2010 | Kreutzer et al. |
| 2010/0003753 A1 | 1/2010 | Guo |
| 2011/0077288 A1 | 3/2011 | Kauppinen et al. |
| 2011/0275785 A1 | 11/2011 | Mixson |
| 2012/0277163 A1 | 11/2012 | Gaur et al. |
| 2013/0177556 A1 | 7/2013 | De Franciscis et al. |
| 2014/0045709 A1 | 2/2014 | Croce et al. |
| 2014/0179758 A1 | 6/2014 | Guo |

FOREIGN PATENT DOCUMENTS

| | | |
|---|---|---|
| JP | 2002/345490 | 12/2002 |
| WO | 07409 | 2/1999 |
| WO | 032619 | 7/1999 |
| WO | 001846 | 1/2000 |
| WO | 44895 | 8/2000 |
| WO | 044914 | 8/2000 |
| WO | 029058 | 4/2001 |
| WO | 036646 | 5/2001 |
| WO | 75164 | 10/2001 |
| WO | 2007069882 | 6/2007 |

OTHER PUBLICATIONS

Written Opinion of the ISA for PCT/US2016/021447 dated Jul. 27, 2016.
Yoo, J. Y.; Pradarelli, J.; Haseley, A.; Wojton, J.; Kaka, A.; Bratasz, A.; Alvarez-Breckenridge, C. A.; Yu, J. G.; Powell, K.; Mazar, A. P. et al. Copper Chelation Enhances Antitumor Efficacy and Systemic Delivery of Oncolytic HSV. Clin. Cancer Res. 2012, 18, 4931-4941.
Abdelmawla, S.; Guo, S.; Zhang, L.; Pulukuri, S. M.; Patankar, P.; Conley, P.; Trebley, J.; Guo, P.; Li, Q. X. Pharmacological Characterization of Chemically Synthesized Monomeric Phi29 Pma Nanoparticles For Systemic Delivery. Mol. Ther. 2011, 19, 1312-1322.
Bartel, David P. "MicroRNAs: genomics, biogenesis, mechanism, and function." cell 116.2 (2004): 281-297.
Bass, Brenda L. "The short answer." Nature 411.6836 (2001): 428-429.
Calin GA, Croce CM MicroRNA signatures in human cancers. Nat Rev Cancer. Nov. 2006;6(11):857-66 doi: 10.1038/nrc1997.
Cheng, Lin, Shideng Bao, and Jeremy N. Rich. "Potential therapeutic implications of cancer stem cells in glioblastoma." Biochemical pharmacology 80.5 (2010): 654-665.

(Continued)

*Primary Examiner* — Kimberly Chong
(74) *Attorney, Agent, or Firm* — Baker Donelson

(57) ABSTRACT

The presently-disclosed subject matter relates to an artificial RNA nanostructure molecule and method to treat brain tumor in a subject. More particularly, the presently disclosed subject matter relates to a RNA nanostructure containing a multiple branched RNA nanoparticle, a brain tumor targeting module, and an effective amount of a therapeutic agent. Further, the presently disclosed subject matter relates to a method of using the RNA nanostructure composition to treat brain tumor in a subject having or at risk of having brain tumor.

28 Claims, 21 Drawing Sheets

Specification includes a Sequence Listing.

(56) References Cited

OTHER PUBLICATIONS

Ciafre, S. A; Galardi, S.; Mangiola, A; Ferracin, M.; Liu, C. G.; Sabatino, G.; Negrini, M.; Maira, G.; Croce, C. M.; Farace, M. G. Extensive Modulation of a Set of Micromas in Primary Glioblastoma. Biochem. Biophys. Res. Commun. 2005, 334, 1351-1358.

Croce, Carlo M. "Causes and consequences of microRNA dysregulation in cancer." Nature reviews genetics 10.10 (2009): 704.

Croce, Carlo M., and George A. Calin. "miRNAs, cancer, and stem cell division." Cell 122.1 (2005): 6-7.

Cui et al. "Regression of Gastric Cancer by Systemic Injection of RNA Nanoparticles Carrying Both Ligand and siRNA," Scientific Reports. Jul. 3, 2015 (Jul. 3, 2015), vol. 5, pp. 1-14. entire document.

Di Leva, Gianpiero, Michela Garofalo, and Carlo M. Croce. "MicroRNAs in cancer." Annual Review of Pathology: Mechanisms of Disease 9 (2014): 287-314.

Elbashir, Sayda M., et al. "Duplexes of 21-nucleotide RNAs mediate RNA interference in cultured mammalian cells." nature 411. 6836 (2001): 494.

Fire, Andrew, et al. "Potent and specific genetic interference by double-stranded RNA in Caenorhabditis elegans." nature 391.6669 (1998): 806-811.

Garzon, Ramiro, George A. Calin, and Carlo M. Croce. "MicroRNAs in cancer." Annual review of medicine 60 (2009): 167-179.

Grapp, M.; Just, I. A.; Linnankivi, T.; Wolf, P.; Lucke, T.; Hausler, M.; Gartner, J.; Steinfeld, R. Molecular Characterization of Folate Receptor 1 Mutations Delineates Cerebral Folate Transport Deficiency. Brain 2012, 135, 2022-2031.

Giiflilhs-Jones, Sam, et al. "miRBase: microRNA sequences, targets and gene nomenclature." Nucleic acids research 34.suppl_1 (2006): D140-D144.

Grodzinski, P.; Torchilin, V.; (Editors) Adv. Drug Delivery Rev.: Cancer Nanotechnology; vol. 66 ed.; Elsevier 2014.

Guo, P. The Emerging Field of RNA Nanotechnology. Nat. Nanotechnol 2010, 5, 833-842.

Guo, P.; Haque, F.; Hallahan, B.; Reif, R.; Li, H. Uniqueness, Advantages, Challenges, Solutions, and Perspectives in Therapeutics Applying RNA Nanotechnology. Nucleic Acid Ther. 2012, 22, 226-245.

Guo, P.; Zhang, C.; Chen, C.; Garver, K.; Trottier, M. Inter-RNA Interaction of Phage Phi29 Pma to Form a Hexameric Complex for Viral DNA Transportation. Mol. Cell 1998, 2, 149-155.

Haque, F.; Shu, D.; Shu, Y.; Shlyakhtenko, L. S.; Rychahou, P. G.; Evers, B. M.; Guo, P. Ultrastable Synergistic Tetravalent RNA Nanoparticles for Targeting to Cancers. Nano Today 2012, 7, 245-257.

Harborth J, Elbashir SM, Bechert K, Tuschl T, Weber K. Identification of essential genes in cultured mammalian cells using small interfering RNAs. J Cell Sci. Dec. 2001;114(Pt 24):4557-65.

Henry, Jon C., Ana Clara P. Azevedo-Pouly, and Thomas D. Schmittgen. "MicroRNA replacement therapy for cancer." Pharmaceutical research 28.12 (2011): 3030-3042.

International Search Report for PCT/US2016/021447 dated Jul. 27, 2016.

Iorio, Marilena V., et al. "MicroRNA gene expression deregulation in human breast cancer." Cancer research 65.16 (2005): 7065-7070.

Jasinski, D. L.; Khisamutdinov, E. F.; Lyubchenko, Y. L.; Guo, P. Physicochemically Tunable Polyfunctionalized RNA Square Architecture With Fluorogenic and Ribozymatic Properties. ACS Nano 2014, 8, 7620-7629.

Khisamutdinov, E. F.; Jasinski, D. L.; Guo, P. RNA as a Boiling-Resistant Anionic Polymer Material to Build Robust Structures With Defined Shape and Stoichiometry. ACS Nano 2014.

Khisamutdinov, E. F.; Li, H.; Jasinski, D. L.; Chen, J.; Fu, J.; Guo, P. Enhancing Immunomodulation on Innate Immunity by Shape Transition Among RNA Triangle, Square and Pentagon Nanovehicles. Nucleic Acids Res. 2014, 42, 9996-10004.

Leamon, C. P.; Parker, M. A; Vlahov, I. R.; Xu, L. C.; Reddy, J. A; Vetzel, M.; Douglas, N. Synthesis and Biological Evaluation of EC20: A New Folate-Derived, (99m)Tc-Based Radiopharmaceutical. Bioconjug. Chem. 2002, 13, 1200-1210.

Lee TJ, Haque F, Shu D, Yoo JY, Li H, Yokel RA, Horbinski C, Kim TH, Kim SH, Kwon CH, Nakano I, Kaur B, Guo P, Croce CM. RNA nanoparticle as a vector for targeted siRNA delivery into glioblastoma mouse model. Oncotarget. Jun. 20, 2015;6(17):14766-76. doi: 10.18632/oncotarget.3632.

Lesniak, M. S.; Brem, H. Targeted Therapy For Brain Tumours. Nat. Rev. Drug Discov. 2004, 3, 499-508.

Li, J.; Zhu, S.; Kozono, D.; Ng, K.; Futalan, D.; Shen, Y.; Akers, J. C.; Steed, T.; Kushwaha, D.; Schlabach, M. et al. Genome-Wide Shma Screen Revealed Integrated Mitogenic Signaling Between Dopamine Receptor D2 (DRD2) and Epidermal Growth Factor Receptor (EGFR) in Glioblastoma. Oncotarget 2014, 5, 882-893.

Liang Z, Wang XJ. Rising from ashes: non-coding RNAs come of age. J Genet Genomics. Apr. 20, 2013;40(4):141-2. doi: 10.1016/j.jgg.2013.03.007. Epub Apr. 8, 2013.

Low, P. S.; Henne, W. A; Doorneweerd, D. D. Discovery and Development of Folic-Acid-Based Receptor Targeting for Imaging and Therapy of Cancer and Inflammatory Diseases. Acc. Chem. Res. 2008, 41, 120-129.

Mao, P.; Joshi, K.; Li, J.; Kim, S. H.; Li, P.; Santana-Santos, L.; Luthra, S.; Chandran, U. R.; Benos, P. V.; Smith, L.; et al. Mesenchymal Glioma Stem Cells Are Maintained by Activated Glycolytic Metabolism Involving Aldehyde Dehydrogenase 1A3. Proc. Natl. Acad. Sci. U.S.A2013, 110, 8644-8649.

Martin-Villalba, A; Okuducu, AF.; Von Deimling, A. The Evolution of Our Understanding on Glioma. Brain Pathol. 2008, 18, 455-463.

Parker, N.; Turk, M. J.; Westrick, E.; Lewis, J. D.; Low, P. S.; Leamon, C. P. Folate Receptor Expression in Carcinomas and Normal Tissues Determined by a Quantitative Radioligand Binding Assay. Anal. Biochem. 2005, 338, 284-293.

Peruzzi, P.; Bronisz, A.; Nowicki, M. O.; Wang, Y.; Ogawa, D.; Price, R.; Nakano, L.; Kwon, C. H.; Hayes, J.; Lawler, S. E. et al. Microma-128 Coordinately Targets Polycomb Repressor Complexes in Glioma Stem Cells. Neuro Oncol. 2013, 15, 1212-1224.

Quintavalle, C.; Donnarumma, E.; Iaboni, M.; Roscigno, G.; Garofalo, M.; Romano, G.; Fiore, D.; De Marinis, P. Croce, C. M.; Condorelli, G. Effect of Mir-21 and Mir-30b/C on TRAIL-Induced Apoptosis in Glioma Cells. Oncogene 2013, 32, 4001-4008.

Quintavalle, C.; Garofalo, M.; Zanca, C.; Romano, G.; Iaboni, M.; Del Basso De Caro, M.; Martinez-Montero, J. C. Incoronato, M.; Nuovo, G.; Croce, C. M et al. Mir-221/222 Overexpression in Human Glioblastoma Increases Invasiveness by Targeting the Protein Phosphate Ptpmu. Oncogene 2012, 31, 858-868.

Rush, D. Periconceptional Folate and Neural Tube Defect. Am. J. Clin. Nutr. 1994, 59, 511S-515S; Discussion 515S-516S.

Sharp, Phillip A. "RNAi and double-strand RNA." Genes & Development 13.2 (1999): 139-141.

Shu, D.; Khisamutdinov, E. F.; Zhang, L.; Guo, P. Programmable Folding of Fusion RNA In Vivo and In Vitro Driven by Pma 3WJ Motif of Phi29 DNA Packaging Motor. Nucleic Acids Res. 2014, 42, E10.

Shu, D.; Moll, W. D.; Deng, Z.; Mao, C.; Guo, P. Bottom-Up Assembly Of RNA Arrays and Superstructures as Potential Parts in Nanotechnology. Nano Lett. 2004, 4, 1717-1723.

Shu, Dan, et al. "Thermodynamically stable RNA three-way junction for constructing multifunctional nanoparticles for delivery of therapeutics." Nature nanotechnology 6.10 (2011): 658.

Shu, Y.; Haque, F.; Shu, D.; Li, W.; Zhu, Z.; Kotb, M.; Lyubchenko, Y.; Guo, P. Fabrication of 14 Different RNA Manoparticles for Specific Tumor Targeting Without Accumulation in Normal Organs RNA 2013, 19, 767-777.

Shu, Yi, et al. "Fabrication of pRNA nanoparticles to deliver therapeutic RNAs and bioactive compounds into tumor cells." Nature protocols 8.9 (2013): 1635.

Shu, Yi, et al. "Stable RNA nanoparticles as potential new generation drugs for cancer therapy." Advanced drug delivery reviews 66 (2014): 74-89.

Steinfeld, R.; Grapp, M.; Kraetzner, R.; Dreha-Kulaczewski, S.; Helms, G.; Dechent, P.; Wevers, R.; Grosso, S.; Gartner, J. Folate Receptor Alpha Defect Causes Cerebral Folate Transport Defi-

(56) References Cited

OTHER PUBLICATIONS ciency: A Treatable Meurodegenerative Disorder Associated With Disturbed Myelin Metabolism. Am. J. Hum. Genet. 2009, 85, 354-363.

Suh, S. S.; Yoo, J. Y.; Nuovo, G. J.; Jeon, Y. J.; Kim, S.; Lee, T. J.; Kim, T.; Bakacs, A.; Alder, H.; Kaur, B. et al. Micrornas/TP53 Feedback Circuitry in Glioblastoma Multiforme. Proc. Natl. Acad. Sci. U.S A 2012, 109, 5316-5321.

Weitman, Steven D., et al. "Distribution of the folate receptor GP38 in normal and malignant cell lines and tissues." Cancer research 52.12 (1992): 3396-3401.

SEQUENCE LISTING

<160> NUMBER OF SEQ ID NOS: 19

<210> SEQ ID NO 1
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uugccaugug uauguggg                                                    18

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cccacauacu uuguugaucc                                                  20

<210> SEQ ID NO 3
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaucaauca uggcaa                                                      16

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cuuacgcuga guacuucgau u                                                21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ucgaaguacu cagcguaagu u                                                21

<210> SEQ ID NO 6
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uugccaugug uaugugggau cccgcggcca uggcggccgg gag                        43

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
gataagctct cccggccgcc atggccgcgg gat                               33
```

<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 8

```
ucuuugguua ucuagcugua ug                                          22
```

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 9

```
uacccuguag aaccgaauuu gug                                         23
```

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 10

```
uucaaguaau ccaggauagg cu                                          22
```

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 11

```
ugagguagua gguuguauag uu                                          22
```

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 12

```
aggcggagac uugggcaauu g                                           21
```

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 13
uggcaguguc uuagcugguu gu                                      22

<210> SEQ ID NO 14
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cguguucaca gcggaccuug au                                      22

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
guccaguuuu cccaggaauc ccu                                     23

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
aacauucauu gcugucggug ggu                                     23

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agcactttct cccggccgcc atggccgcgg gat                          33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atttgcacct cccggccgcc atggccgcgg gat                          33

<210> SEQ ID NO 19
<211> LENGTH: 39
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 19
uugccaugug uauguggggcu uacgcugagu acuucgauu                                39
```

RNA NANOPARTICLES FOR BRAIN TUMOR TREATMENT

RELATED APPLICATIONS

This application is a Divisional Application of U.S. application Ser. No. 15/554,360, which issued as U.S. Pat. No. 10,584,144 on Mar. 10, 2020, which is a § 371 National Stage Application of PCT/US2016/021447 filed Mar. 9, 2016, which claims the benefit of U.S. Provisional Patent Application No. 62/130,459, filed Mar. 9, 2015, the entire disclosures of which are hereby incorporated by reference in their entireties.

GOVERNMENT INTEREST

This invention was made with government support under CA151648 (P.G.), EB012135 (P.G.), CA152758 (C.M.C.), CA175875 (I.N.), CA163205 (I.N.), P30NS045758 (B.K.), R01064607 (B.K.), R01CA150153 (B.K.), and P01CA163205 (B.K.) awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 30, 2018, is named 2935720-7_SL.txt and is 4,791 bytes in size.

TECHNICAL FIELD

The presently-disclosed subject matter relates to an artificial RNA nanostructure molecule and method to treat brain tumor in a subject. More particularly, the presently disclosed subject matter relates to a RNA nanostructure containing a multiple branched RNA nanoparticle, a brain tumor targeting module, and an effective amount of a therapeutic agent. Further, the presently disclosed subject matter relates to a method of using the RNA nanostructure composition to treat brain tumor in a subject having or at risk of having brain tumor.

INTRODUCTION

The most common primary brain tumors in adults are glioblastomas, which are also one of the most deadly cancers (1). For glioblastomas, conventional treatment involves surgical resection followed by radiation and concurrent chemotherapy. Even with this treatment regimen, the median survival of patients with glioblastoma is less than 15 months. The poor prognosis is primarily due to tumor recurrence, which is thought to originate from a subset of cancer stem cells that survive the primary treatments. Recent studies suggested that glioblastoma stem cell survived the therapeutic stresses and become more aggressive when they recur, developing resistance to the primary chemotherapy.

Bacterial virus phi29 DNA packaging RNA (pRNA) molecule is a crucial component in the phi29 DNA packaging motor and contains two functional domains. The intermolecular interaction domain is located at the central region (bases 23-97) and within this domain there are two loops (right hand loop and left hand loop) which are responsible for the hand-in-hand interaction through the four complementary base sequences within these two loops. The other domain is a DNA translocation domain which is located at the 5'/3' paired ends. The right hand loop (bases 45-48) and the left hand loop (bases 82-85) allow for the formation of pRNA dimers, trimers and hexamer rings via intermolecular base-pairing via the interaction of two interlocking loops, the pRNA molecules form dimers, trimers, hexamers, and patterned superstructures [7]. This property of forming self-assembled nanostructure makes pRNA ideal building blocks for bottom-up assembly. RNA nanotechnology has been rapidly growing as a new generation platform for biological and medical application (2-3). As nanotechnology rapidly evolves, many attempts have been made to deliver small interfering RNA (siRNA) using viruses, liposome, lipid, and polymer based nanoparticles (4).

Clearly there remains a need for improved composition and methods targeting both brain tumor cells and glioblastoma stem cells to treat the primary brain tumor and prevent tumor recurrence is desired. The presently disclosed subject matter relates to RNA nanoparticle containing compositions useful for prophylactic and therapeutic treatment for brain tumors.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. This Summary does not list or suggest all possible combinations of such features.

In some embodiments, the presently disclosed subject matter provides an artificial RNA nanostructure molecule. The molecule includes a multiple branched RNA junction motif comprising at least one RNA oligonucleotide, and a brain tumor targeting module, and the module is coupled to an RNA junction motif. In some embodiments, the molecule further includes at least one bioactive agent coupled to the RNA junction motif. A non-limiting example of the bioactive agent is a therapeutic agent. In some embodiments, the RNA oligonucleotide is at least 6 nucleotides in length. In some embodiments, the RNA oligonucleotide includes at least one chemical modification at the 2' position. Non-limiting examples of the chemical modification include 2'Fluoro, 2' Amine, 2'O-Methyl, or a combination thereof.

In some embodiments, the multiple branched RNA includes a nucleotide sequence 5'-UUG CCA UGU GUA UGU GGG AUC CCG CGG CCA UGG CGG CCG GGA G-3' (SEQ ID NO: 6). In some embodiments, the multiple branched RNA includes a sequence 5'-GATAAGCT CTC CCG GCC GCC ATG GCC GCG GGA T-3' (SEQ ID NO: 7). In some embodiments, the multiple branched RNA junction motif is a three-branched RNA junction motif. In some embodiments, the three-branched RNA junction motif includes a packaging RNA (pRNA) three-way junction (3WJ) motif. In some embodiments of the present disclosure, the RNA molecules form dimers, trimers, hexamers, and patterned superstructures.

In some embodiments, the presently disclosed subject matter provides that a branch of the three-branched RNA junction motif includes an a3WJ RNA module. In some embodiments, a branch of the three-branched RNA junction motif includes a b3WJ RNA module. In some embodiments, a branch of the three-branched RNA junction motif includes a c3WJ RNA module. In some embodiments, the three-branched RNA junction motif includes an a3WJ RNA module, a b3WJ RNA module, and a c3WJ RNA module. A non-limiting example of RNA module include nucleotide sequences 5'-UUG CCA UGU GUA UGU GGG-3' (SEQ ID NO: 1), 5'-CCC ACA UAC UUU GUU GAUCC-3' (SEQ ID NO: 2), and 5'-GGA UCA AUC AUG GCA A-3' (SEQ ID NO: 3).

In some embodiments, the diameter of the molecule is at least about 40 nm or less. In some embodiments, the diameter of the molecule is at least about 30 nm or less. In some embodiments, the diameter of the molecule is at least about 15 nm or less.

In some embodiments, the RNA molecule has a zeta potential ranging from about −50 mV to about 50 mV. In some embodiments, the molecule has a zeta potential ranging from about −25 my to about 25 mV.

In some embodiments, the presently disclosed subject matter provides that the brain tumor targeting module in the artificial RNA nanostructure molecule includes a ligand that binds to at least one brain tumor cell surface marker. Non-limiting examples of the brain tumor surface marker includes folate receptor, EGFR, transferrin receptor, and an RGD. In some embodiments, the ligand includes an aptamer. In some embodiments, the aptamer binds to EGFR, PDGFR, folate receptor, or a combination thereof. In some embodiments, In some embodiments, the targeting module is a folate.

In some embodiments, the presently disclosed subject matter provides a bioactive agent includes a drug, a fluorescent dye, a chemical, or a combination thereof. In some embodiments, the bioactive agent includes a siRNA, a miRNA, an anti-miRNA, a ribozyme RNA, an antisense RNA, or a combination thereof. In some embodiments, the bioactive agent is directed to a brain tumor marker. Non-limiting examples of the bioactive agent include siRNA sequence and microRNA sequence. In some embodiments, the microRNA molecule is at least 3 nucleotide in length. In some embodiments, the bioactive agent is an anti-miRNA molecule for a miRNA encoding miR-9, miR-10b, miR-21, miR-17, or miR-26. In some embodiments, the bioactive agent is a miRNA molecule for a miRNA encoding let-7a, miR-10b, miR-25, miR-34a, miR-124, miR-145, or miR-181b. In some embodiments, the miRNA includes miRNA locked nucleic acid (LNA) molecule. In some embodiments, the microRNA sequence is an anti-miR-21 sequence. In some embodiments, non-limiting examples of the miRNA sequence comprises 5'-GATAAGCT-3',5'-AGCACTTT-3', or 5'-ATTTGCAC-3'. In some embodiments, the miRNA includes an miRNA locked nucleic acid (LNA) molecule. In some embodiments, the bioactive agent includes a LNA miRNA molecule 5'-+G+A+T+A+A+G+C+T-3'. In some embodiments, miRNA LNA molecule includes a sequence 5'-+A+G+C+A+C+T+T+T-3'. In some embodiments, miRNA LNA molecule includes a sequence 5'-+A+T+T+T+G+C+A+C-3'.

In some embodiments, the microRNA is a locked nucleic acid (LNA) sequence. In some embodiments, the microRNA is a LNA-miR21 sequence 5'-+G+A+T+A+A+G+C+T-3'. In some embodiments, the siRNA binds to a mRNA sequence of a gene that promotes tumorigenesis, angiogenesis, cell proliferation, or a combination thereof, in the brain or spinal cord. In some embodiments, the siRNA binds to a mRNA molecule that encodes a protein including pro-tumorigenic pathway proteins, pro-angiogenesis pathway proteins, pro-cell proliferation pathway proteins, anti-apoptotic pathway proteins, or a combination thereof. In further embodiments, the mRNA molecule encodes a protein including but not limited to VEGF pathway proteins, EGFR pathway proteins, MGMT pathway proteins, Raf1 pathway proteins, MMP pathway proteins, mTOR pathway proteins, TGFβ pathway proteins, or Cox-2 pathway proteins, or a combination thereof. In some embodiments, non-limiting examples of protein include VEGF, EGFR, POK, AKT, AGT, RAF, RAS, MAPK, ERK, MGMT, MMP-2, MMP-9, PDGF, PDGFR, IGF-I, HGF, mTOR, Cox-2 and TGFβ1. In some embodiments, the siRNa binds to a mRNA molecule that encodes RAS, cMET, HER2, MDM2, PIK3CA, AKT, CDK4, or a combination thereof.

Further provided, in some embodiments of the presently disclosed subject matter, is a nucleic acid composition. The composition includes a therapeutically effective amount of the artificial RNA nanostructure molecule as disclosed above. In some embodiments, the composition includes a pharmaceutically acceptable carrier.

Still further, the presently disclosed subject matter, in some embodiments, provides a nanoparticle delivery system. The delivery system includes the artificial RNA nanostructure molecule as disclosed above. In some embodiments, the nanoparticle delivery system further includes a pharmaceutically acceptable carrier.

In another aspect, the presently disclosed subject matter provides, in some embodiments, a method of treating a brain tumor in a subject having or at risk of developing a brain tumor. The method includes administering to the subject a therapeutically effective amount of a composition comprising an artificial RNA nanostructure molecule as disclosed herein. In some embodiments, the composition includes a pharmaceutically acceptable carrier. In some embodiments, the subject is a mammal or a non-mammal vertebrate. In some embodiments, the subject is a human. In some embodiments, the brain tumor is glioblastoma.

Further, in some embodiments, the present disclosure provides a method of preventing brain tumor recurrence a subject having or at risk of having brain tumor recurrence. The method includes administering to the subject a therapeutically effective amount of a composition comprising an artificial RNA nanostructure molecule as disclosed herein. In some embodiments, the composition includes a pharmaceutically acceptable carrier. In some embodiments, the subject is a mammal or a non-mammal vertebrate. In some embodiments, the subject is a human. In some embodiments, the brain tumor is glioblastoma.

BRIEF DESCRIPTION OF THE DRAWINGS

The features of the presently disclosed subject matter are set forth with particularity in the appended claims. A better understanding of the features and advantages of the presently disclosed subject matter will be obtained by reference to the following detailed description that sets forth illustrative embodiments, in which the principles of the subject matter are used, and the accompanying drawings of which. The drawings were originally published in color, incorporated by reference in their entireties (Tae Jin Lee, et al. (2015) *Oncotarget*, Vol. 6, No. 17, 14766-14776). The black and white drawings of the instant application correspond to the color ones published.

FIG. 1A discloses SEQ ID NOS 19, 3, 2 and 5, respectively, in order of appearance. B, Atomic force microscopy (AFM) image showing three-branched triangular structure of self-assembled trivalent FA-pRNA-3WJ-si(Luc) RNP. C, Dynamic light scattering (DLS) data showing the size of FA-pRNA-3WJ-si(Luc) RNP. D, Zeta potential of FA-pRNA-3WJ-si(Luc) RNP. The data in C and D were obtained from three independent experiments.

DESCRIPTION OF EXEMPLARY EMBODIMENTS

Figure 1:
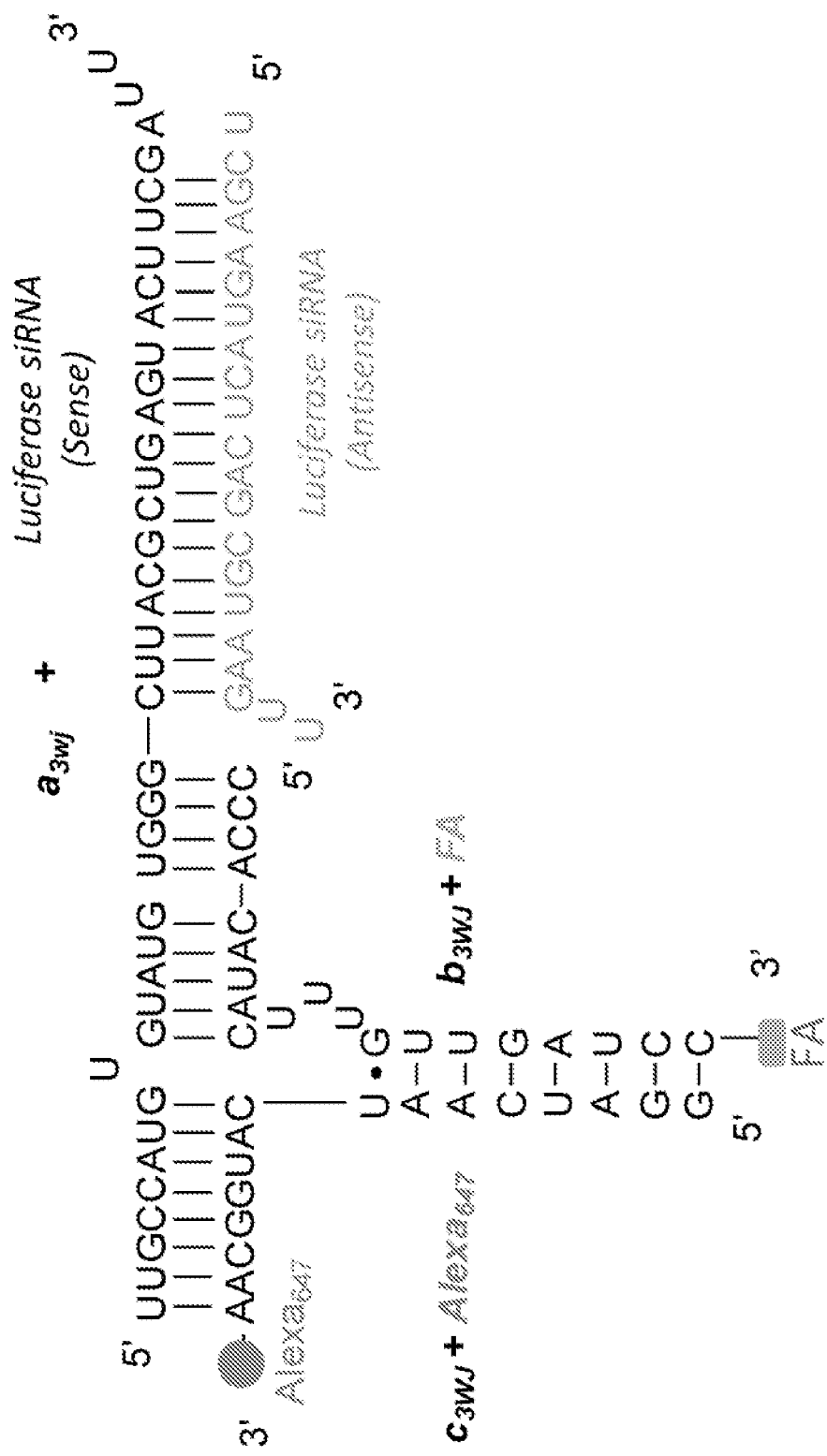
FIG. 1, panels A-D are diagrams and images illustrating construction and characterization of multi-functional pRNA-3WJ RNP for glioblastoma cell targeting. A, Construction map of trivalent FA-Alexa647-pRNA-3WJ-si(Luc) RNP harboring three functionalities to form: Folate (FA) as a targeting ligand; Alexa647 as an imaging module; and luciferase siRNA for gene silencing.
Figure 1:
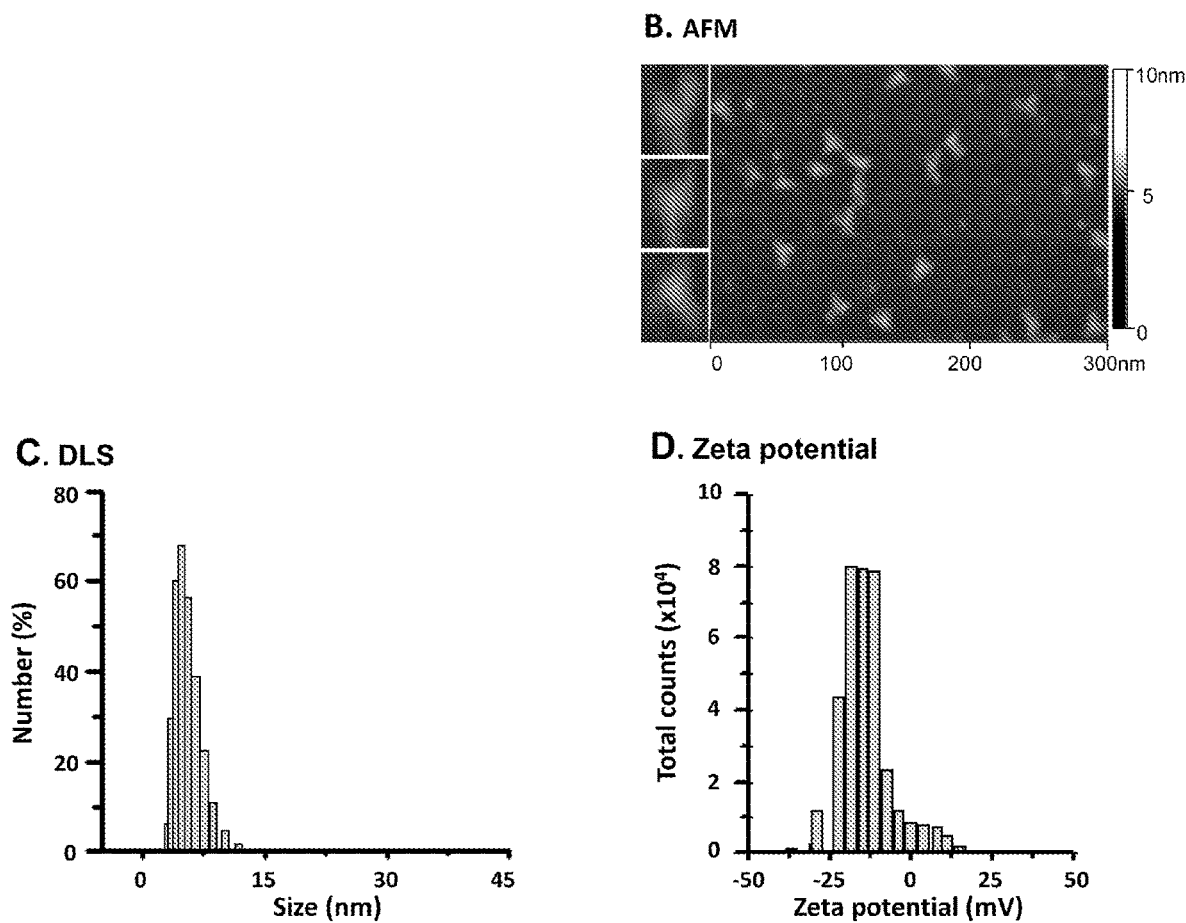

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter relates to RNA nanostructure molecule and method to treat brain tumor in a subject. More particularly, the presently disclosed subject matter relates to a molecule containing a multiple branched RNA junctive motif, a brain tumor targeting module. Further, the presently disclosed subject matter relates to a method of using the RNA nanostructure composition to treat brain tumor in a subject having or at risk of having brain tumor.

In some embodiments, the presently disclosed subject matter provides an artificial RNA nanostructure molecule. The molecule includes a multiple branched RNA junction motif comprising at least one RNA oligonucleotide, and a brain tumor targeting module, and the module is coupled to an RNA junction motif. In some embodiments, the molecule further includes at least one bioactive agent coupled to the RNA junction motif. In some embodiments, the RNA oligonucleotide is at least about 6 nucleotides in length.

RNA nanotechnology has recently emerged as an important field due to recent finding of its high thermodynamic stability, favorable and distinctive in vivo attributes (US 2014/0179758, hereby incorporate by reference in its entirety). In some embodiments of the present disclosure, as disclosed in US2014/0179758, the RNA molecules form dimers, trimers, hexamers, and patterned superstructures. Further, RNA nanoparticles can be fabricated with precise control of shape, size and stoichiometry, as demonstrated by the packaging RNA (pRNA) of the bacteriophage phi29 DNA packaging motor, which forms dimmers, trimers, and hexamers via hand-in-hand interactions of the interlocking loops.

In some embodiments, the presently disclosed subject matter relates to a RNA nanoparticle based composition. Such nanoparticles is delivered systemically and specifically target intracranial tumors with minimal toxicity. In some embodiments, the nanoparticle relates to a pRNA three-way junction (pRNA-3WJ). The pRNA-3WJ of the bacteriophage phi29 DNA packaging motor can be used to fabricate a RNA nanoparticle (RNP) with precise control of shape, size and stoichiometry (4-10). Creation of boiling resistant RNPs with controllable shapes and defined stoichiometry has been recently reported (11).

The term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

In some embodiments, the RNA oligonucleotide of the RNA nanoparticles includes at least one chemical modification at the 2' position. Non-limiting examples of the chemical modification include 2'Fluoro, 2' Amine, 2'O-Methyl, or a combination thereof. In one embodiments, the pRNA-3WJ nanoparticles with 2'-Fluoro (2'-F) modifications of U and C nucleotides renders the RNPs resistant to RNase degradation enhancing their in vivo half-life while retaining authentic functions of the incorporated modules (7, 12, 13). Furthermore, the pRNA-3WJ RNPs were non-toxic, non-immunogenic, and displayed favorable biodistribution and pharmacokinetic profiles in mice (14). These favorable characteristics make this novel platform attractive for the systemic delivery of siRNA to glioblastoma. One promising ligand for nanoparticle therapy in glioblastoma targeting is folate, a natural member of the B-vitamin family. Folate is required for early neuronal development and differentiation (15). Its transportation across the blood-cerebrospinal fluid barrier (BCSF) occurs by the choroid plexus (16). The choroid plexus expresses the largest amount of folate receptor (FR) in a body, while no FR expression is detected in cerebellum, cerebrum or spinal cord (17, 18).

In some embodiments, the multiple branched RNA includes a nucleotide sequence 5'-UUG CCA UGU GUA UGU GGG AUC CCG CGG CCA UGG CGG CCG GGA G-3' (SEQ ID NO: 6). In some embodiments, the multiple branched RNA includes a sequence 5'-GATAAGCT CTC CCG GCC GCC ATG GCC GCG GGA T-3' (SEQ ID NO: 7). In some embodiments, the presently disclosed subject matter provides that a branch of the three-branched RNA junction motif includes an a3WJ RNA module. In some embodiments, a branch of the three-branched RNA junction motif includes a b3WJ RNA module. In some embodiments, a branch of the three-branched RNA junction motif includes a c3WJ RNA module. In some embodiments, the three-branched RNA junction motif includes an a3WJ RNA module, a b3WJ RNA module, and a c3WJ RNA module. A non-limiting example of RNA module include nucleotide sequences 5'-UUG CCA UGU GUA UGU GGG-3' (SEQ ID NO: 1), 5'-CCC ACA UAC UUU GUU GAUCC-3' (SEQ ID NO: 2), and 5'-GGA UCA AUC AUG GCA A-3' (SEQ ID NO: 3).

In some embodiments, the diameter of the molecule is at least about 40 nm or less. The diameter is at least about 35 nm or less, at least about 30 nm or less, at least about 25 nm or less, at least 20 nm or less, at least 15 nm or less, at least 10 nm or less, at least 5 nm or less.

In some embodiments, the molecule has zeta potential ranging from about −150 mV to about 150 mV. The RNA molecule has a zeta potential ranging from about −140 mV to about 140 mV, from about −130 mV to about 130 mV, from about −120 mV to about 120 mV, from about −110 mV to about 110 mV, from about −100 mV to about 100 mV, from about −90 to about 90 mV, form about −80 mV to about 80 mV, from about −70 mV to about 70 mV, from about −60 mV to about 60 mV. In some embodiments, the RNA molecule has a zeta potential ranging from about −50 mV to about 50 mV. The molecule has a zeta potential ranging from about −45 my to about 45 mV, from about −40 mV to about 40 mV, from about −35 mV to about 35 mV, from about −35 mV to about 30 mV, from about −35 mV to about 20 mV, from about −25 mV to about 15 mV.

In some embodiments, the RNA nanostructure molecule is substantially stable in pH ranges from about 2 to about 13. The RNA molecule is substantially stable in pH about 2, 3, 4, 5, 6, 7, 8, 9, 10, 11, 12 and 13. As used herein, the term "substantially stable" can refer to physical and/or chemical stability. As will be recognized by those of ordinary skill in the art, the term "substantially stable" can refer to stability of the composition under certain conditions, relative to an initial composition (i.e., when a particular batch of the composition is initially prepared). In this regard, as will be recognized by those of ordinary skill in the art, one manner in which stability of a particular embodiment of the composition can be determined is as follows: preparing a batch of the embodiment of the composition, making an initial assessment of a sample of the composition (control sample), subjecting a sample of the composition to conditions of interest (e.g., storage at a particular temperature for a particular time period) (test sample), making an assessment of the test sample, and comparing the assessment of the control sample to the assessment of the test sample. Calculations can be made to determine whether the amounts present in the test sample are 100%±20, 19, 18, 17, 16, 15, 14, 13, 12, 11, 10, 9, 8, 7, 6, 5, 4, 3, 2, 1, 0.5, or 0.1% of the amount that is in the control sample.

In some embodiments, the presently disclosed subject matter provides that the brain tumor targeting module in the artificial RNA nanostructure molecule includes a ligand that binds to at least one brain tumor cell surface marker. As used herein, cell surface markers include any cellular component that may be detected within or on the surface of a cell, or a macromolecuie bound or aggregated to the surface of the cell. As such, cell surface markers are not limited to markers physically on the surface of a cell. For example, cell surface markers may include, but are not limited to surface antigens, transmembrane receptors or coreceptors, macromolecules bound to the surface, such as bound or aggregated proteins or carbohydrates, internal cellular components, and the like. Non-limiting examples of the brain tumor surface marker includes folate receptor, EGFR, transferrin receptor, and an RGD. In some embodiments, the ligand includes an aptamer. In some embodiments, the aptamers binds against EGFR, PDGFR, or folate receptor. In some embodiments, the targeting module is a folate.

In some embodiments, a brain tumor targeting module is coupled to the RNA nanoparticle. The targeting module direct the nanoparticle to the brain tumor cells, to enhance binding to them, to enhance internalization, to enhance targeting to cellular enzymes, DNA, RNA, proteins, lipids, or carbohydrates. Non-limiting examples of the brain tumor targeting module are antibodies, antibody fragments, polypeptides, cell ligands, aptamers, DNA, RNA, drugs, compounds that enhance targeting the brain tumor cell, and other groups or materials that enhance binding to brain tumor cells.

In some embodiments, a brain tumor targeting module may be an antibody. The antibody may have an ability to recognize and specifically bind to a target on tumor cells and tissues. Non-limiting example of the antibody is an antibody configured to specifically bind a protein selected from but not limited to EGFR, human epidermal growth factor (HER), laminin 411, insulin-like growth factor (IGF) and tumor necrosis factor-alpha (INF-a).

In some embodiments, a targeting module is an antibody of a class described as antagonist antibodies, which specifically bind to a brain tumor stem cell marker protein and interfere with, for example, ligand binding, receptor dimerization, expression of a brain tumor stem cell marker protein, and/or downstream signaling of a cancer stem cell marker protein. Yet in other embodiments, a targeting module is an antibody of a class described as agonist antibodies which specifically bind to a brain tumor stem cell marker protein and promote, for example, ligand binding, receptor dimerization, and/or signaling by a cancer stem cell marker protein. Yet in further embodiments, a targeting module is an antibody that does not interfere with or promote the biological activity of a brain tumor stem cell marker protein and may instead function to inhibit tumor growth by, for example, antibody internalization and/or recognition by the immune system.

In some embodiments, the targeting module may include a lectin or another ligand specific to the transferrin receptor. A brain tumor targeting module may further e a ligand to one of any number of cell surface receptors or antigens, such as RGD.

Further examples of the targeting module is a chemical molecule, a small drug molecule or a chromophore molecule, or a protein molecule, or a lectin that are covalently joined to polymaleic acid in constructing the conjugation with the RNA nanoparticle.

The term "folate" as used herein can comprise, for example, a genus of well-defined B-vitamin compounds, including but not limited to, 5-methyltetrahydro folate, 5-formyltetrahydrofolate, dihydrofolate, tetrahydrofolate, folic acid and other folate compounds. Since folate is an essential component required during DNA replication and methylation in highly proliferating cells, many cancer cells, such as those of the brain, ovary, lung, breast, kidney, endometrium, colon and bone marrow, over-express FRs to increase folate uptake (19). Folic acid (FA), a synthetic oxidized form of folate, has been widely used as a ligand in various cancer targeting materials (20).

In some embodiments, the presently disclosed subject matter provides a bioactive agent includes a drug, a fluorescent dye, a chemical, or a combination thereof. In some embodiments, the bioactive agent includes an imaging module. Non-limiting examples of the imaging module is fluorescent dye, including a non-limiting example Alexa647. In some embodiments, the bioactive agent is coupled to the RNA nanostructure molecule. In some embodiments, the bioactive agent is a therapeutic agent. In some embodiments, the bioactive agent includes a siRNA, a miRNA, an anti-miRNA, a ribozyme RNA, an antisense RNA, or a combination thereof. In some embodiments, the bioactive agent is directed to a brain tumor marker. Non-limiting examples of the bioactive agent include siRNA sequence and microRNA sequence.

RNA interference (RNAi) is a polynucleotide sequence-specific, post-transcriptional gene silencing mechanism effected by double-stranded RNA that results in degradation of a specific messenger RNA (mRNA), thereby reducing the expression of a desired target polypeptide encoded by the mRNA (see, e.g., WO 99/32619; WO 01/75164; U.S. Pat. No. 6,506,559; Fire et al., Nature 391:806-11 (1998); Sharp, Genes Dev. 13:139-41 (1999); Elbashir et al. Nature 411: 494-98 (2001); Harborth et al., J. Cell Sci. 114:4557-65 (2001)). RNAi is mediated by double-stranded polynucleotides as also described hereinbelow, for example, double-stranded RNA (dsRNA), having sequences that correspond to exonic sequences encoding portions of the polypeptides for which expression is compromised.

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. In one embodiment, the siRNA comprises a double stranded polynucleotide molecule comprising complementary sense and antisense regions, wherein the antisense region comprises a sequence complementary to a region of a target nucleic acid molecule (for example, a nucleic acid molecule encoding BRCAA1). In another embodiment, the siRNA comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

In some embodiments, the siRNA molecule of the presently disclosed subject matter is a siRNA molecule that binds to a single stranded RNA molecule, which is a messenger RNA (mRNA) that encodes at least part of a peptide or protein whose activity promotes tumorigenesis, angiogenesis, or cell proliferation in the brain or spinal cord of a mammal, or which is a microRNA (miRNA) whose activity promotes tumorigenesis, angiogenesis, or cell proliferation in the brain or spinal cord of a mammal. In some embodiment of the present disclosure, to interfere oncogenic coding genes to regress brain tumor growth, the RNA nanostructure molecule silence oncogenes, including but not limited to, RAS, cMET, HER2, MDM2, PIK3CA, AKT, and CDK4.

The phrase "brain tumor marker" as used herein refers to genes or gene products (e.g., RNA molecules or proteins) which are characteristic of some or all of the cells in brain cancer. A brain cancer marker with diagnostic value can be a gene or gene product expressed in normal, non-cancerous cells, but is characteristic of a type or classification of cancer by, for example, its over-expression or under-expression as compared to its expression in normal, non-cancerous cells. A brain tumor marker with prognostic value is a gene or gene product for which the over-expression or under-expression confers predictive information about the future aggressiveness of a cancer and/or its response to therapy at the time of diagnosis. In a cancer sample, the patterns of expression of diagnostic and prognostic cancer markers allow one to accurately identify and determine the future course of the disease, respectively. Non-limiting examples of brain tumor biomarkers are described in WO2007069882 (herein incorporated by reference in its entirety).

In one embodiment, the siRNA molecule binds to an mRNA that encodes at least part of a peptide or protein whose activity promotes tumorigenesis, angiogenesis, or cell proliferation, or a combination thereof, in the brain or spinal cord of a mammal. Such may be the case when the mRNA molecule encodes a protein in a pro-tumorigenic pathway, pro-angiogenesis pathway, pro-cell proliferation pathway, or anti-apoptotic pathway. For example, the protein can be a VEGF pathway protein, EGFR pathway protein, MGMT pathway protein, RAF pathway protein, MMP pathway protein, mTOR pathway protein, TGFβ pathway protein, or Cox-2 pathway protein. In one embodiment, the protein is one of the following, including but not limited to, VEGF, EGFR, PDK, AKT, AGT, RAF1, RAS, MAPK, ERK, MGMT, MMP-9, PDGF, PDGFR, IGF-I, HGF mTOR, Cox-2, or TGFβ1. In another embodiment, the protein is VEGF, EGFR, MGMT, MMP-2, MMP-9, or PDGF. In still another embodiment, the protein is RAFI, mTOR, Cox-2, or TGFβ1.

In some embodiments, the present disclosure provides that the bioactive agent is a microRNA sequence. As used herein, the term "MicroRNAs (miRNAs)" as used herein are single-stranded, or double stranded non-coding RNAs, at least about 6 nucleotide in length that can regulate gene expression at the post-transcriptional level by either degrading their target mRNAs or inhibiting their translation (See, e.g. Bartel, D. P., (2004), Cell, 116,281-297; Liang Z., et al., (2013), J Genet. Genomics, 40, 141-142). MiRNAs play important roles in regulating cell cycle, proliferation, differentiation, metabolism, and apoptosis. A compendium of microRNA and respective microRNA binding sequences is available at the miRNA registry. (See, e.g., Griffiths-Jones et al. (2006) Nucl. Acids Res. 34:D140-D144, US20140045709, herein incorporate by reference in their entireties.) In particular embodiments, the microRNA and microRNA binding sequence employed in the present disclosure are associated with a disease or condition, wherein an antagonist or agonist to the microRNA would be useful in preventing or treating the disease or condition. Dysregulation of miRNAs has been implicated in tumor initiation, progression, and metastasis in several cancer types (See, Carlin G. A., et al., *Nat. Rev. Cancer* 2006, 6, 857-866; Di L. G., et al., *Annu. Rev. Pathol.* 2014, 9, 287-314; Garzon, R. et al., *Annu. Rev. Med.* 2009, 60, 167-179; Iorio, M. V., et al., *Cancer Res* 2005, 65, 7065-7070; Croce, C. M., et al., *Cell* 2005, 122, 6-7.). MiRNAs hold great potentials for cancer therapy particularly because one miRNA can regulate a broad set of target genes efficiently and simultaneously, and can therefore address the heterogeneous nature of cancer. Naturally occurring miRNA further displays reduced immune response and low toxicity. Both anti-miRNAs to knockdown oncogenic miRNAs and mimics of miRNAs to upregulate endogenous miRNAs have been developed as therapeutic strategies to achieve tumor regression (Henry, J., et al. *Pharm Res* 2011, 28, 3030-3042). However, the major limiting factor is the ability to specifically deliver these therapeutic modules to affected cells and tissues. Nanotechnology holds great promise in this regard and several nanoplatforms have been pursued, but effective strategies to inhibit tumor progression are still lacking (Grodzinski, P.; Torchilin, V.; (Editors) *Adv. Drug Delivery Rev.: Cancer Nanotechnology*; Volume 66 ed.; Elsevier: 2014.).

In some embodiments, the microRNA or anti-miRNA sequence is at least about 3 nucleotide in length. In some embodiments, the miRNA molecule has a length of at least 3, 4, 5, 6, 7, 8, 9, 10, 11, 12, 13, 14, 15, 16, 17, 18, 19, 20, 21, 22, 23, 24, 25, 26, 27, 28, 29, 30 nucleotides or more. IN some embodiments, an anit-miRNA or an antagomir of a miRNA molecule is at least about 6 nucleotides in length. In some embodiments, the antagomir of a miRNA molecule has a length of at least about 3, 4, 5, 6, 7, 8, 9, 10, 11, 12, 13, 14, 15, 16, 17, 18, 19, 20, 21, 22, 23, 24, 25, 26, 27, 28, 29, 30 nucleotides or more.

In some embodiments, to interfere oncogenic miRNA to regress brain tumor growth, the RNA nanostructure molecule contains anti-miRNA that silences oncogenic miRNAs, including but not limited to, miR-9, miR-10b, miR-21, miR-17, and miR-26. In some embodiments, to rescue down-regulated tumor suppressive miRNAs, RNA nanostructure introduces includes tumor suppressive miRNAs, including but not limited to, let-7a, miR-10b, miR-25, miR-34a, miR-124, miR-145, and miR-181b. MiRNA sequences are listed below:

```
miR-9:
                                    (SEQ ID NO: 8)
5'-UCUUUGGUUA UCUAGCUGUA UG-3' miR-10b:
                                    (SEQ ID NO: 9)
5'-UACCCUGUAGAACCGAAUUUGUG-3' miR-26a:
                                    (SEQ ID NO: 10)
5'-UUCAAGUAAUCCAGGAUAGGCU-3' let-7a:
                                    (SEQ ID NO: 11)
5'-UGAGGUAGUAGGUUGUAUAGUU-3' miR-25:
                                    (SEQ ID NO: 12)
5'-AGGCGGAGACUUGGGCAAUUG-3' miR-34a:
                                    (SEQ ID NO: 13)
5'-UGGCAGUGUCUUAGCUGGUUGU-3' miR-124:
                                    (SEQ ID NO: 14)
5'-CGUGUUCACAGCGGACCUUGAU-3' miR-145:
                                    (SEQ ID NO: 15)
5'-GUCCAGUUUUCCCAGGAAUCCCU-3' miR-181b:
                                    (SEQ ID NO: 16)
5'-AACAUUCAUUGCUGUCGGUGGGU-3'
```

In some embodiments, the microRNA includes a locked nucleic acid (LNA) sequence. In some embodiments, the microRNA is a LNA-anti-miR21 sequence

```
                                    (SEQ ID NO: 7)
5'-+G+A+T+A+A+G+C+T

CTC CCG GCC GCC ATG GCC GCG GGA T-3'
```

(underlined sequence is 8-mer anti-miR21 LNA, and "+" denotes LNA sequence). In some embodiments, the RNA nanostructure contains a strand LNA17_sph1: 5'-+A+G+C+A+C+T+T+TCTCCCGGCCGCCATGGCCGCGGGAT-3' (SEQ ID NO: 17) ("+" denotes LNA sequence.) In another embodiment, the RNA nanostructure contains a strand of LNA19a_sph1: 5'-+A+T+T+T+G+C+A+CCTCCCGGCCGCCATGGCCGCGGGAT-3' (SEQ ID NO: 18) ("+" denotes LNA sequence.).

In some embodiments, the present disclosure provides inhibitors of miRNAs (e.g., anti-miR-21). Compositions comprising such inhibitors and methods for inhibiting miR-21 using such inhibitors are also disclosed herein. Any miRNA inhibitor may be used alone, or with other miRNA inhibitor(s) known in the art. In some embodiments, the miRNA inhibitor comprises an antisense molecule. In some embodiments, the antisense molecule could be a single or a double stranded sequence. Examples of antisense molecule include, but are not limited to, siRNAs, triple-helix-forming agents, ribozymes, RNAi, synthetic peptide nucleic acids (PNAs), antigenes (agRNAs), LNA/DNA copolymers, small molecule chemical compounds, and antisense oligonucleotides.

Further provided, in some embodiments of the presently disclosed subject matter, is a nucleic acid composition. The composition includes a therapeutically effective amount of the artificial RNA nanostructure molecule as disclosed above. In some embodiments, the composition includes a pharmaceutically acceptable carrier.

Still further, the presently disclosed subject matter, in some embodiments, provides a nanoparticle delivery system. The delivery system includes the artificial RNA nanostructure molecule as disclosed above. In some embodiments, the nanoparticle delivery system further includes a pharmaceutically acceptable carrier.

In another aspect, the presently disclosed subject matter provides, in some embodiments, a method of treating a brain tumor in a subject having or at risk of developing a brain tumor. The method includes administering to the subject a therapeutically effective amount of a composition comprising an artificial RNA nanostructure molecule as disclosed above and herein. In some embodiments, the composition includes a pharmaceutically acceptable carrier.

Further, in some embodiments, the present disclosure provides a method of preventing brain tumor recurrence a subject having or at risk of having brain tumor recurrence. The method includes administering to the subject a therapeutically effective amount of a composition comprising an artificial RNA nanostructure molecule as disclosed above and herein. In some embodiments, the composition includes a pharmaceutically acceptable carrier.

Brain tumors are a very serious and are among the most difficult to treat, with a very short survival in patients, despite administration of the optimal treatment available. The very unique biological environment of the brain, as separated by the blood-cerebrospinal fluid barrier (BCFB), significantly contributes to a range of site-specific cancers in this organ that require alternative treatment than those cancers of the remaining human body. Treatment consists primarily of surgical removal and radiation therapy; chemotherapy is also used, but the range of suitable chemotherapeutic agents is limited, perhaps because most therapeutic agents do not penetrate the blood-brain barrier adequately to treat brain tumors. Using known chemotherapeutics along with surgery and radiation rarely extends survival much beyond that produced by surgery and radiation alone. Thus improved therapeutic options are needed for brain tumors.

In some embodiments, the brain tumor is a glioma. Gliomas are a common type of brain tumor. They arise from the supportive neuronal tissue comprised of glial cells (hence the name glioma), which maintain the position and function of neurons. In some embodiments, gliomas are classified according to the type of glial cells they resemble: astrocytomas (including glioblastomas) resemble star-shaped astrocyte glial cells, oligodendrogliomas resemble oligodendrocyte glial cells; and ependymomas resemble ependymal glial cells that form the lining of fluid cavities in the brain. In some embodiments, a tumor may contain a mixture of these cell types, and would be referred to as a mixed glioma.

As disclosed herein, in some embodiments, the brain tumor is a glioblastoma. Glioblastomas is the most common primary brain tumors in adults and are also one of the most deadly cancers (1). The median survival of patients with glioblastoma is less than 15 months. The poor prognosis is primarily due to tumor recurrence, which is thought to originate from a subset of cancer stem cells that survive the primary treatments. Recent studies suggested that glioblastoma stem cell survived the therapeutic stresses and become more aggressive when they recur, developing resistance to the primary chemotherapy. In some embodiment, the presently disclosed subject matter provides a method of administering the RNA nanostructure composition as disclosed herein to both brain tumor cells and glioblastoma stem cells to treat the primary brain tumor and prevent tumor recurrence.

In some embodiments, the method(s) as disclosed herein includes administering to the subject a therapeutically effective amount a composition. The composition includes an artificial RNA nanostructure molecule, wherein the molecule includes a multiple branched RNA junction motif comprising at least one RNA oligonucleotide, a brain tumor targeting module coupled to an RNA junction motif, and at least one therapeutic agent coupled to the RNA junction motif. In some embodiments, the composition further includes a pharmaceutically acceptable carrier. In some embodiments, the bioactive agent comprises a therapeutic agent. In some embodiments, the RNA oligonucleotide comprises at least one chemical modification at the 2' position. Non-limiting examples of the modification comprises 2'Fluoro, 2' Amine, 2'O-Methyl, or a combination thereof. In some embodiments, the motif is a three-branched RNA junction motif. An non-limiting example of the three-branched RNA junction motif comprises a packaging RNA (pRNA) three-way junction (3WJ) motif. In some embodiments, the diameter of the molecule is at least about 40 nm or less. In some embodiments, the molecule has a zeta potential ranging from about −50 mV to about 50 mV. In some embodiments, the multiple branched RNA includes a nucleotide 5'-UUG CCA UGU GUA UGU GGG AUC CCG CGG CCA UGG CGG CCG GGA G-3' (SEQ ID NO: 6). In another embodiment, the multiple branched RNA comprises sequence 5'-GATAAGCT CTC CCG GCC GCC ATG GCC GCG GGA T-3' (SEQ ID NO: 7). In some embodiments, a branch of the three-branched RNA junction motif includes at least one of an a3WJ RNA module (SEQ ID NO: 1); a b3WJ RNA module (SEQ ID NO: 2); or a c3WJ RNA module (SEQ ID NO: 3).

In some embodiments, the brain tumor targeting module in the method(s) of the presently disclosed subject matter includes a ligand that binds to at least one brain tumor cell surface marker. In some embodiments, the ligand binds to a folate receptor, an EGFR, a transferrin receptor, an RGD, or a combination thereof. In some embodiments, the ligand comprises an aptamer. In some embodiments, the targeting module comprises a folate. Non-limiting examples of folate include folic acid, 5-methyltetrahydro folate, 5-formyltetrahydrofolate, dihydrofolate, tetrahydrofolate, or other folate compounds.

In some embodiments, the therapeutic agents in the method(s) of the presently disclosed subject matter includes a drug, a fluorescent dye, a chemical, or a combination thereof. Further, the therapeutic agent includes a siRNA, a miRNA, an anti-miRNA, a ribozyme RNA, an antisense RNA, or a combination thereof. In some embodiments, the therapeutic agent is directed to a brain tumor marker. In some embodiments, the therapeutic agent is a siRNA sequence, or a microRNA sequence. In some embodiments, the microRNA sequence is at least 6 nucleotide in length. Non-limiting example of the microRNA is a locked nucleic acid (LNA) sequence. An example of the LNA sequence is a LNA-miR21 sequence as described herein. In some embodiments, the siRNA binds to a mRNA sequence of a gene that promotes tumorigenesis, angiogenesis, cell proliferation, or a combination thereof, in the brain or spinal cord. In some embodiments, the siRNA binds to a mRNA molecule that encodes a protein including pro-tumorigenic pathway proteins, pro-angiogenesis pathway proteins, pro-cell proliferation pathway proteins, anti-apoptotic pathway proteins, or a combination thereof. In some embodiments, the mRNA molecule encodes a protein including VEGF pathway proteins, EGFR pathway proteins, MGMT pathway proteins, Raf1 pathway proteins, MMP pathway proteins, mTOR pathway proteins, TGFβ pathway proteins, or Cox-2 pathway proteins, or a combination thereof. In some embodiments, the protein includes VEGF, EGFR, POK, AKT, AGT, RAF, RAS, MAPK, ERK, MGMT, MMP-2, MMP-9, PDGF, PDGFR, IGF-I, HGF, mTOR, Cox-2 or TGFβ1.

Further, in some embodiments of the methods, the present subject matter relates to a method to target and deliver therapeutic siRNA to brain tumors using FA-conjugated pRNA-3WJ RNP. First, intracranial tumor xenograft models in mice was established and then systemically administered RNPs through the tail vein. Based on fluorescence imaging, It is demonstrated that the pRNA-3WJ RNP efficiently targeted and internalized into brain tumor cells through FR-mediated endocytosis with little or no accumulation in adjacent healthy brain cells. Gene silencing by the RNPs was also demonstrated within the luciferase gene expressing brain tumors. More importantly, pRNA-3WJ RNPs were also capable of targeting brain tumor stem cells derived from a human patient. The data demonstrate that artificially engineered RNPs can specifically target brain tumor cells, including glioblastoma stem cells, and deliver functional siRNA and therapeutic microRNAs (miRNAs) (21).

The term "treatment" and "prophylaxis" as used herein is to be considered in its broadest context. The term "treatment" does not necessarily imply that a host is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of onset of a particular condition. "Treatment" may also reduce the severity of an existing condition.

The term "pharmaceutically acceptable carrier" as used herein refers to a diluent, adjuvant, excipient, or vehicle with which a heterodimeric probe of the disclosure is administered and which is approved by a regulatory agency of the federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable, or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. When administered to a patient, the heterodimeric probe and pharmaceutically acceptable carriers can be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol, and the like. The present compositions, if desired, can also contain minor amounts of wetting or emulsifying agents, or pH buffering agents. The present compositions advantageously may take the form of solutions, emulsion, sustained release formulations, or any other form suitable for use.

The term "therapeutically effective amount," as used herein, refers to the amount of a composition containing administered to a patient already suffering from a disease, condition, or disorder, sufficient to cure or at least partially arrest, or relieve to some extent one or more of the symptoms of the disease, disorder, or condition being treated. The effectiveness of such compositions depend upon conditions including, but not limited to, the severity and course of the disease, disorder, or condition, previous therapy, the patient's health status and response to the drugs, and the judgment of the treating physician. By way of example only, therapeutically effective amounts may be determined by routine experimentation, including but not limited to a dose escalation clinical trial.

The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "subject" refers to a target of administration of the pharmaceutical composition. The subject of the herein disclosed methods can be a vertebrate, such as a mammal, a fish, a bird, a reptile, or an amphibian. Thus, the subject of the herein disclosed methods can be a human or non-human. Thus, veterinary therapeutic uses are provided in accordance with the presently disclosed subject matter. As such, the presently disclosed subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. The term does not denote a particular age or sex.

Suitable methods for administering to a subject an effective amount of the composition in accordance with the methods of the present invention include but are not limited to systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

The particular mode of drug administration used in accordance with the methods of the present invention depends on various factors, including but not limited to the vector and/or drug carrier employed, the severity of the condition to be treated, and mechanisms for metabolism or removal of the drug following administration.

The presently-disclosed subject matter is further illustrated by the following specific but non-limiting examples. The following examples may include compilations of data that are representative of data gathered at various times during the course of development and experimentation related to the presently disclosed subject matter.

EXAMPLES

Example 1

Glioblastoma is one of the most deadly cancers. Systemic siRNA administration to treat glioblastoma patients requires a robust and efficient delivery platform without immunogenicity. This example report the application of RNA nanotechnology based on pRNA 3-way-junction (3WJ) of bacteriophage phi29 for glioblastoma targeting. Multivalent folate (FA)-conjugated RNA nanoparticles were constructed to harbor siRNA. The resulted FA-pRNA-3WJ RNA nanoparticle (RNP) specifically targeted and entered human malignant glioblastoma cells in vitro and intracranial glioblastoma xenografts in vivo. Systemically injected FA-pRNA-3WJ RNPs successfully targeted and delivered siRNA into brain tumor cells in mice, and efficiently reduced luciferase reporter gene expression (4-fold lower than control). The FA-pRNA-3WJ RNA nanoparticles were also demonstrated to target both human patient-derived glioblastoma stem cells, which are thought to be responsible for tumor initiation, drug resistance and deadly recurrence, and the derived brain tumor in mouse model without accumulation in adjacent normal brain cells, nor other major internal organs. The results of this study may promise a successful clinical application of pRNA-3WJ RNP for specific delivery of therapeutics such as siRNA, microRNA and/or chemotherapeutic drugs into glioblastoma cells without inflicting collateral damage to healthy tissues.

Results and Discussion

This study was to assess application of pRNA-3WJ RNP for systemic delivery of therapeutic RNA, such as siRNA and miRNA, into brain tumors in a mouse model system. For targeted delivery of siRNA into brain tumors, a multifunctional RNP was constructed, as previously described (7, 12, 13, 22), using a scaffold based on pRNA sequences of phi29 bacteriophage with slight modifications (see Materials and Methods). Three RNA modules individually transcribed in vitro or synthesized chemically were mixed at equal molar ratio and formed three-branched RNP via one-step self-assembly. Each RNA module was designed to carry a functional moiety: 1) FA as the FR targeting ligand; 2) fluorophore Alexa647 as the imaging agent; and 3) luciferase siRNA as the gene silencing functional moiety or scrambled RNA as a negative control (FIG. 1A) (7, 12, 13, 22). The resulting RNP was named FA-pRNA-3WJ-si(luc) RNP. Observation of the self-assembled FA-pRNA-3WJ-si(luc) RNP under atomic force microscopy (AFM) revealed the formation of homogeneous three-branched architectures with 3WJ core in the center (FIG. 1B), confirming the previous reports that modifications on each RNA module did not abrogate the shape-controlled self-assembly to retain the pRNA-3WJ core structure essential for homogeneous uniformed RNP formation. Dynamic light scattering (DLS) determined average hydrodynamic diameters of FA-pRNA-3WJ-si(luc) RNP to be 5.2±1.2 nm (FIG. 1C), which was smaller than the predicted size (10×4×2 nm) calculated by RNA folding software based on expected duplex helix parameters and base pair lengths of the three individual RNA modules. The discrepancy between DLS measurement and computational prediction implies that each protruded branch of FA-pRNA-3WJ-si(luc) RNP was avoided from averaging three dimensions due to rapid motion of nanoparticles in solution. Another factor that needs to be addressed for successful systemic in vivo application of nanoparticles is freedom from aggregation to avoid rapid clearance from the body and diminished specific interaction between the conjugated ligand and cellular target receptors. Aggregation depends largely on the surface charge of nanoparticles and the surface of RNA is indeed highly charged. Aggregation will also change the surface charge proportional to the extent of size increase. To determine the aggregation extent, FA-pRNA-3WJ-si(luc) RNP was subjected to zeta potential analysis to measure the particle surface charge. Zeta potential of FA-pRNA-3WJ-si(luc) RNP in PBS solution was measured as a single peak at −15.8±5.6 mV (FIG. 1D), indicating that most FA-pRNA-3WJ-si(luc) RNP exist as a single form without aggregation. These physical properties favor the FA-pRNA-3WJ-si(luc) RNP for systemic in vivo application.

Figure 2:
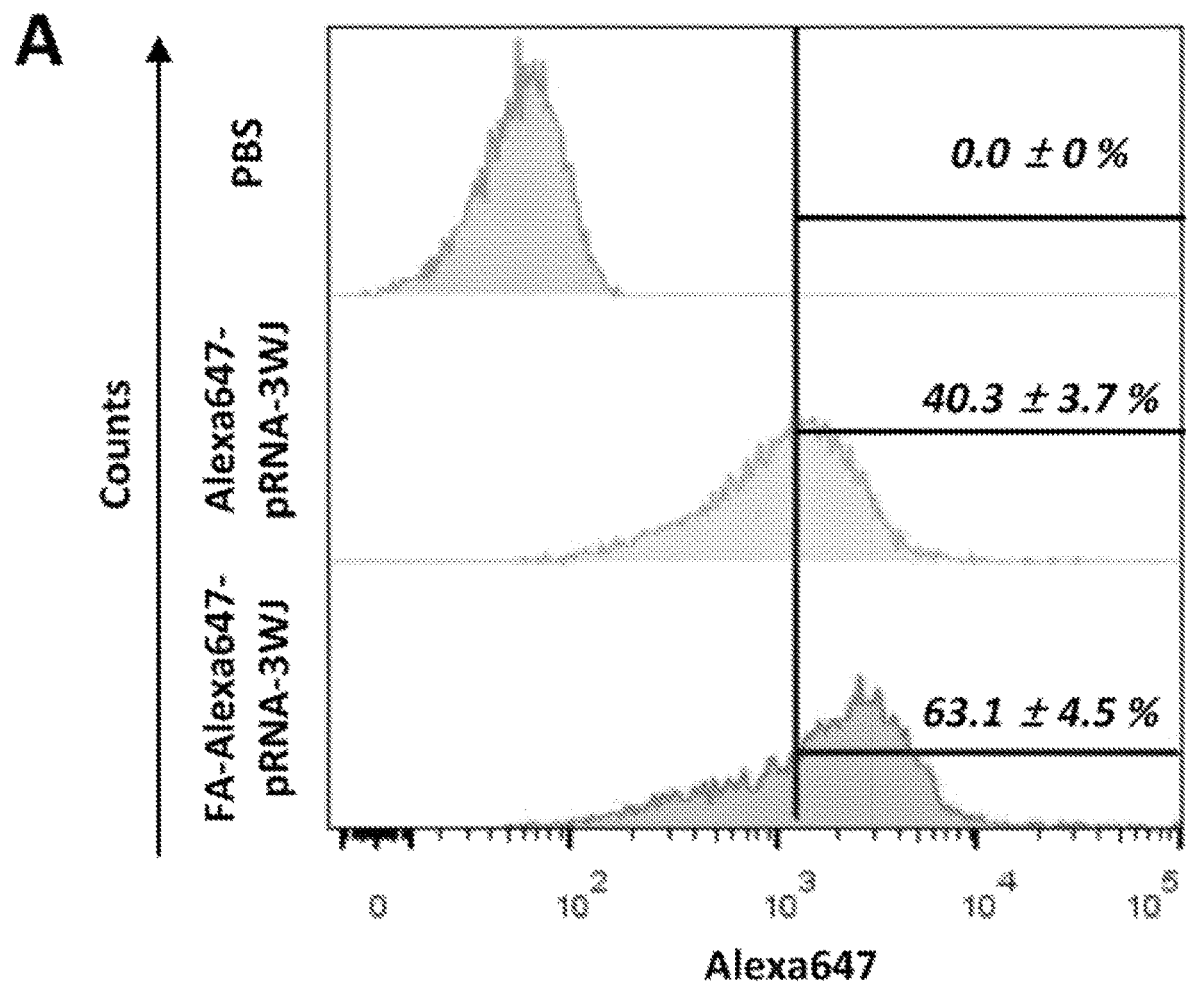
FIG. 2, panels A-D are graphs and images showing FA-mediated human glioblastoma cell targeting by FA-Alexa647-pRNA-3WJ RNP in vitro and in vivo. A, Flow cytometry analysis for FA-dependent human glioblastoma cell U87EGFRvIII targeting in vitro by FA-Alexa647-pRNA-3WJ RNP. Alexa647 signals from U87EGFRvIII cells treated with 200 nM of FA-Alexa647-pRNA-3WJ RNP were compared to control RNP (FA-free Alexa647-pRNA-3WJ RNP) normalized to PBS control. Percentage of cell populations were analyzed by student t-test ($p<0.001$, $n=4$). B, Immunofluorescence confocal microscopy for FA-dependent human glioblastoma cell U87EGFRvIII targeting in vitro by FA-Alexa647-pRNA-3WJ RNP (middle) in comparison to control RNP (FA-free Alexa647-pRNA-3WJ) (top) or 1 mM free folate pre-treated cells in culture media (bottom). Pseudocolor was used for nucleus (blue), cytoskeleton (green) and Alexa647 (red). C, U87EGFRvIII-induced brain tumors in mice targeted by FA-Alexa647-pRNA-3WJ RNP. Tumors were determined by MM (yellow arrows in top panel) and visualized by fluorescence in vivo imaging (bottom panel) after tail vein injection of FA or FA-free Alexa647-pRNA-3WJ RNP. Representative images from each group of 4 were displayed. D, ANOVA analysis on fluorescence intensity of Alexa647 normalized by tumor volume ($mm^3$), $p=0.019$ ($n=4$).
Figure 2:
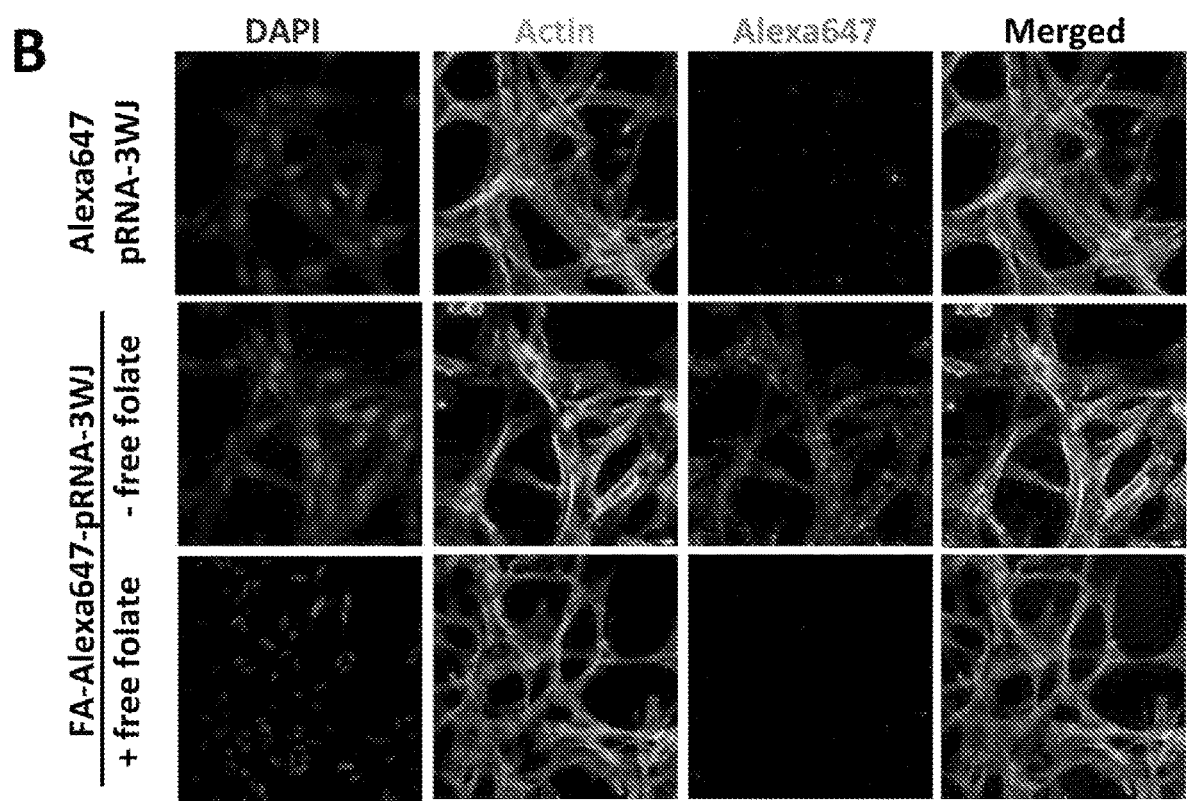
Figure 2:
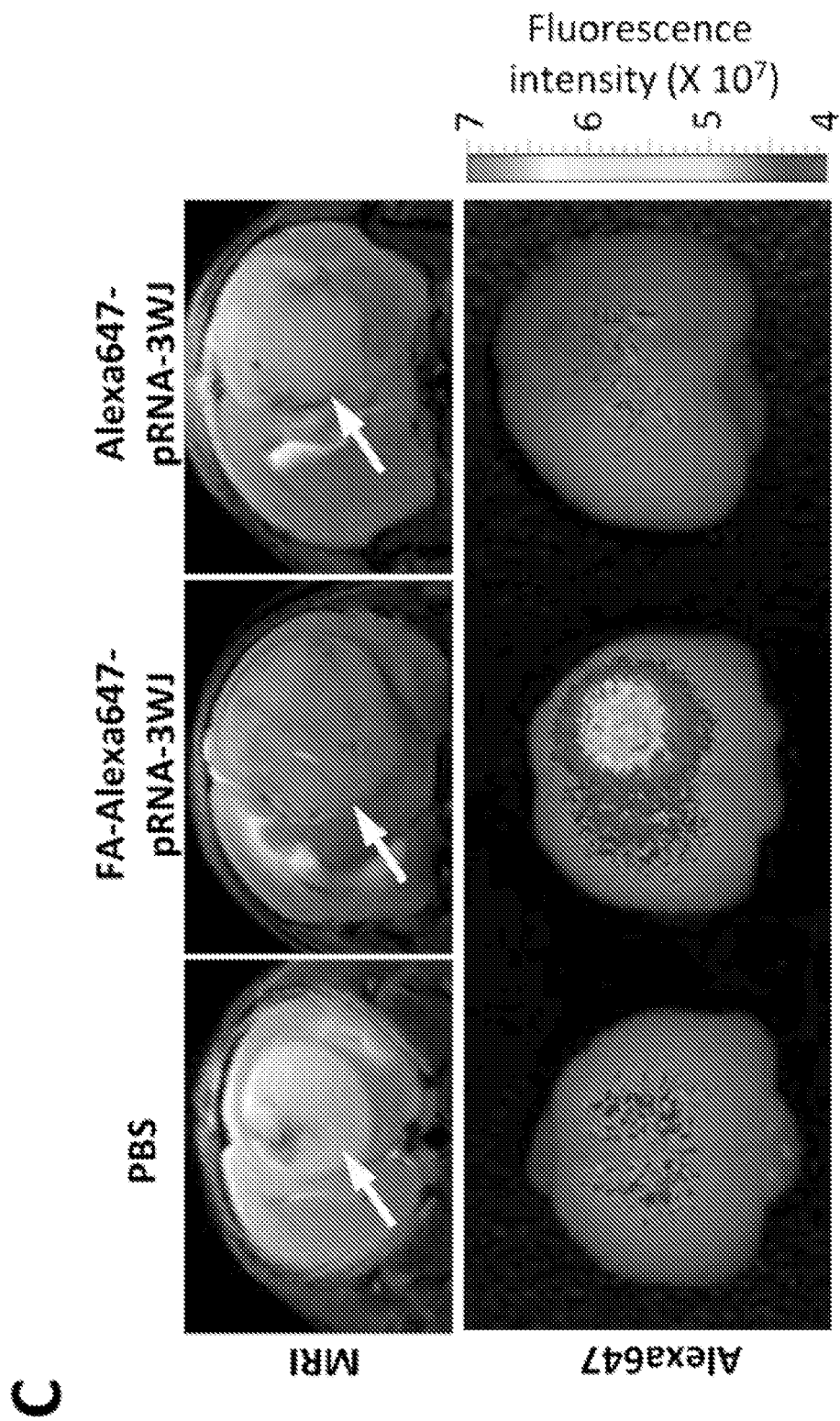
Figure 2:
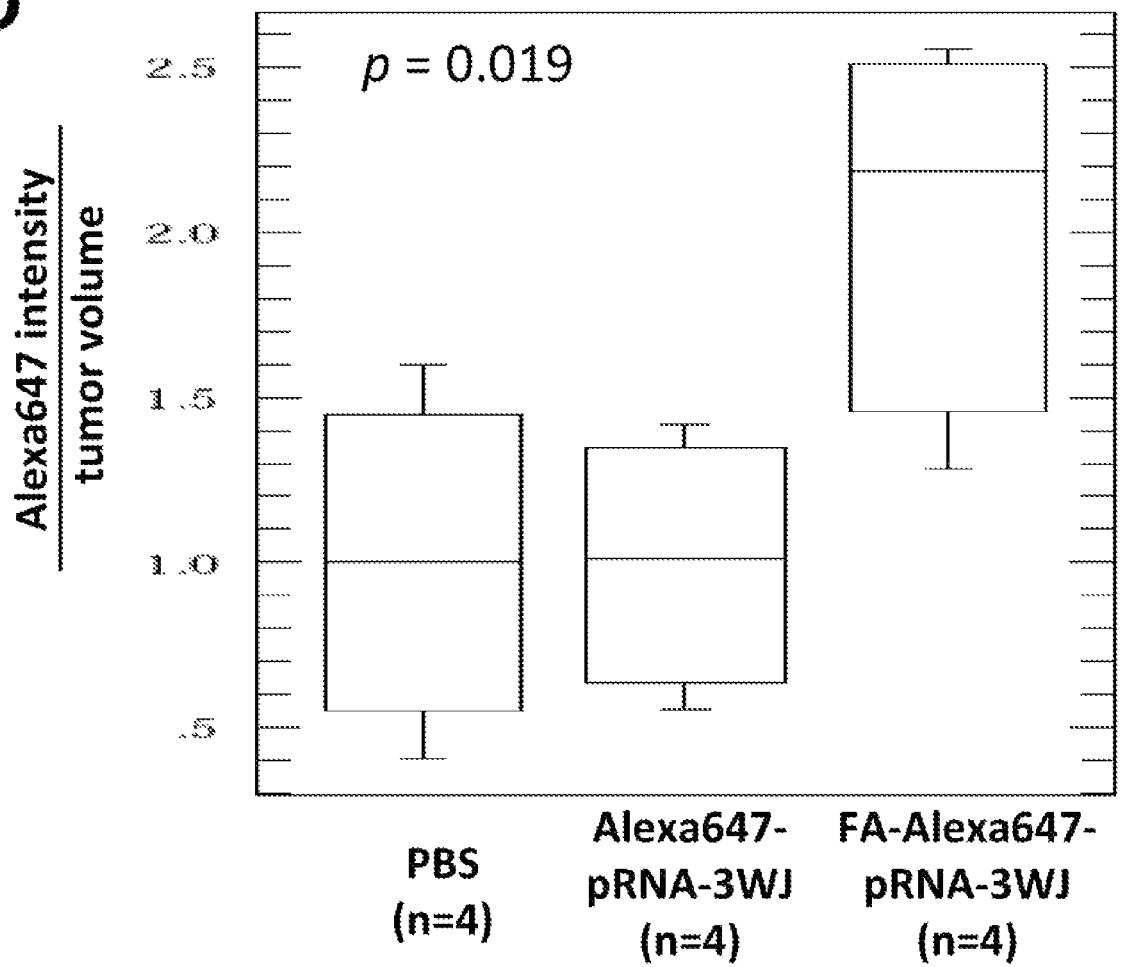
Figure 5:
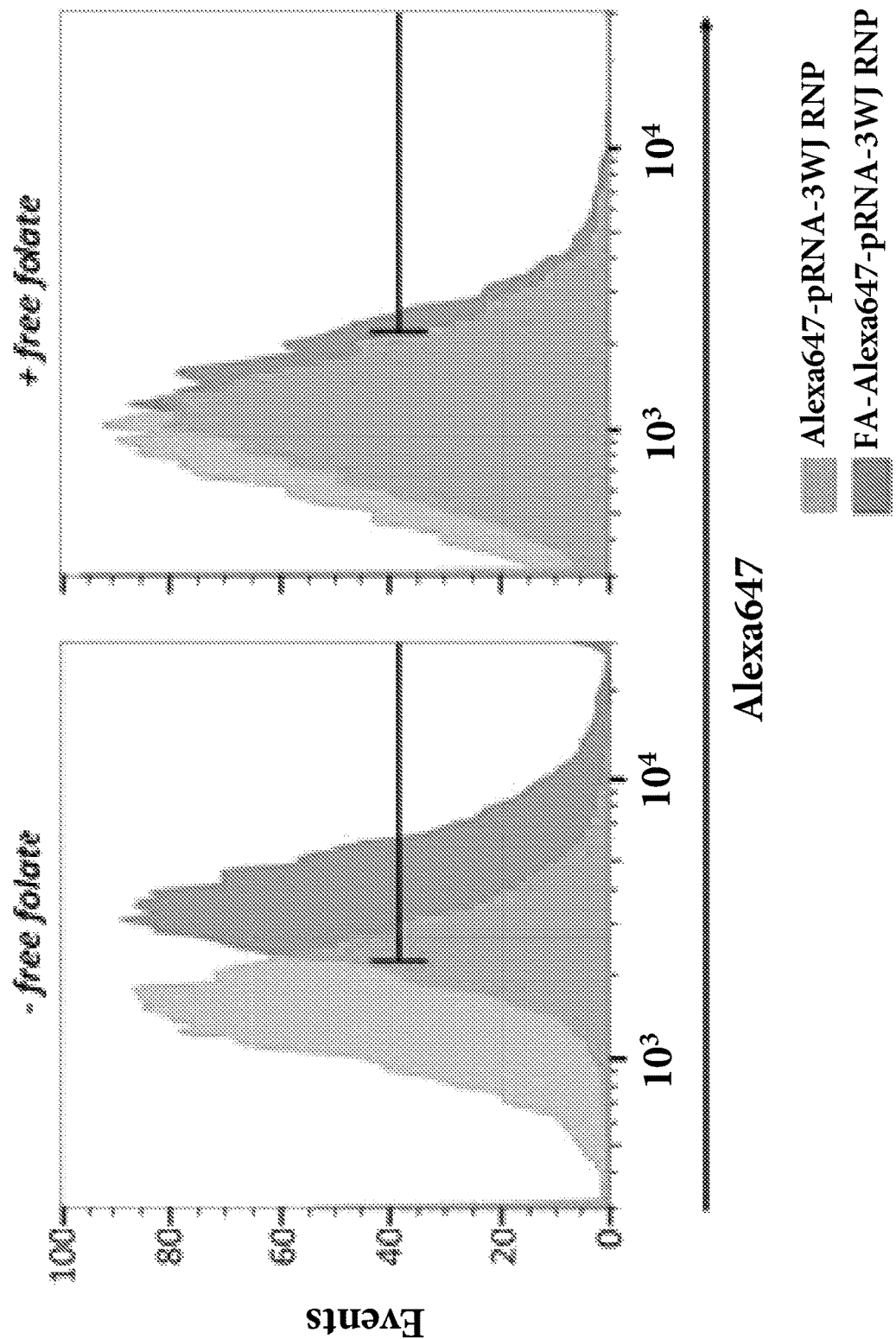
FIG. 5 is graphs illustrating flow cytometry analysis for FA-mediated human glioblastoma cell targeting by FA-Alexa647-pRNA-3WJ RNP in vitro. Human glioblastoma cells U87EGFRvIII were pre-treated with 1 mM free folate in culture media for 1 hr before incubation with FA-Alexa647-pRNA-3WJ RNP containing medium. Events as a function of Alexa647 signal intensity detected from U87EGFRvIII cells treated with 200 nM of FA-Alexa647-pRNA-3WJ RNP were compared to control RNP (FA-free Alexa647-pRNA-3WJ RNP). The figure is representative of three experiments.
Figure 6:
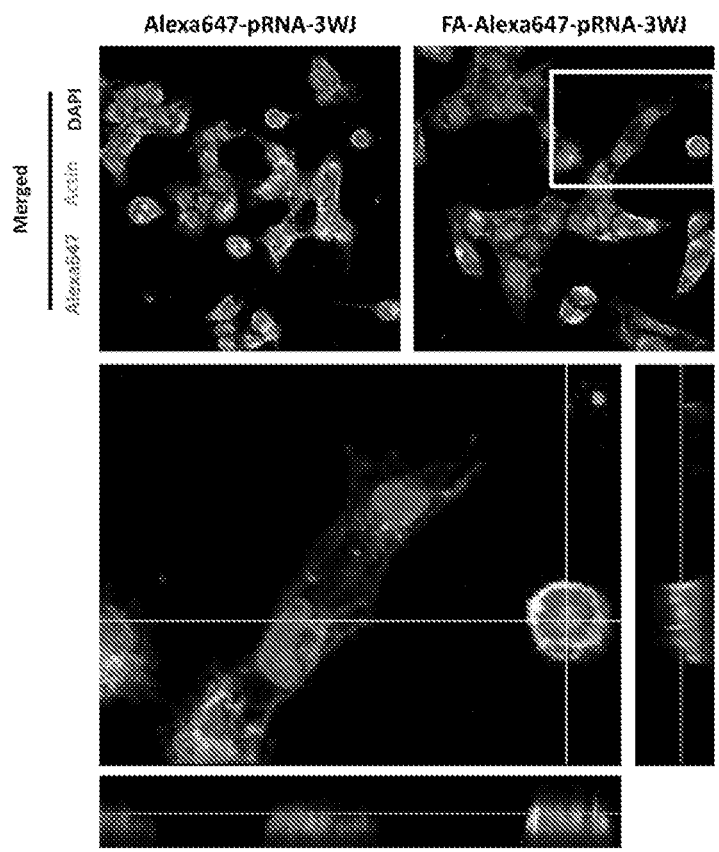
FIG. 6 contains images showing FA-mediated human glioblastoma cell T98G in vitro targeting by FA-Alexa647-pRNA-3WJ RNPs. Glioblastoma multiforme (GBM) cell line, T98G, was treated with 200 nM of FA-Alexa647-pRNA-3WJ or Alexa647-pRNA-3WJ for 1 hr, followed by fluorescence confocal microscopy. Pseudocolor was used for nuclear (blue), cytoskeleton (green) and Alexa647 (red).

Human glioblastoma cells are known to overexpress FR, while normal brain cells show no FR expression (17-19). To determine the specific recognition and binding capability of FA-pRNA-3WJ-si(luc) RNP towards human glioblastoma cells, firstly association of FA-Alexa647-pRNA-3WJ with U87EGFRvIII cell was tested in vitro in comparison to FA-free control RNP (Alexa647-pRNA-3WJ). Flow cytometry analysis showed a higher association of FA-Alexa647-pRNA-3WJ with U87EGFRvIII cells (63.1±4.5%) than that of Alexa647-pRNA-3WJ (40.3±3.7%) (student t-test, p<0.001, n=4) (FIG. 2A). When FRs of U87EGFRvIII cells were pre-masked by incubating with 1 mM free-folate for 1 hr of culture before the RNP binding, the association between FA-Alexa647-pRNA-3WJ and U87EGFRvIII cells was decreased to an extent similar to the negative control Alexa647-pRNA-3WJ (FIG. 5), indicating that the association between FA-Alexa647-pRNA-3WJ and U87EGFRvIII cells was FR dependent. The FR-mediated specific binding of FA-Alexa647-pRNA-3WJ to U87EGFRvIII cells was further confirmed by visualizing the Alexa647 signal from surface-cultured U87EGFRvIII cells treated with FA-Alexa647-pRNA-3WJ RNP under confocal fluorescence microscope. Higher fluorescence intensity of Alexa647 dye was observed from U87EGFRvIII cells treated with FA-Alexa647-pRNA-3WJ than those with control RNP (Alexa647-pRNA-3WJ) (FIG. 2B). Again, the FA-dependent association of FA-Alexa647-pRNA-3WJ RNP was abolished by pre-treatment of U87EGFRvIII cells with 1 mM free folate in culture medium (FIG. 2B). The FR-mediated specific association between FA-Alexa647-pRNA-3WJ RNP and human glioblastoma cell was also observed with other glioblastoma cell lines including T98G (FIG. 6). Taken together, FA-conjugated pRNA-3WJ RNP has the capability to recognize and bind to human brain tumor cells through FR.

Figure 7:
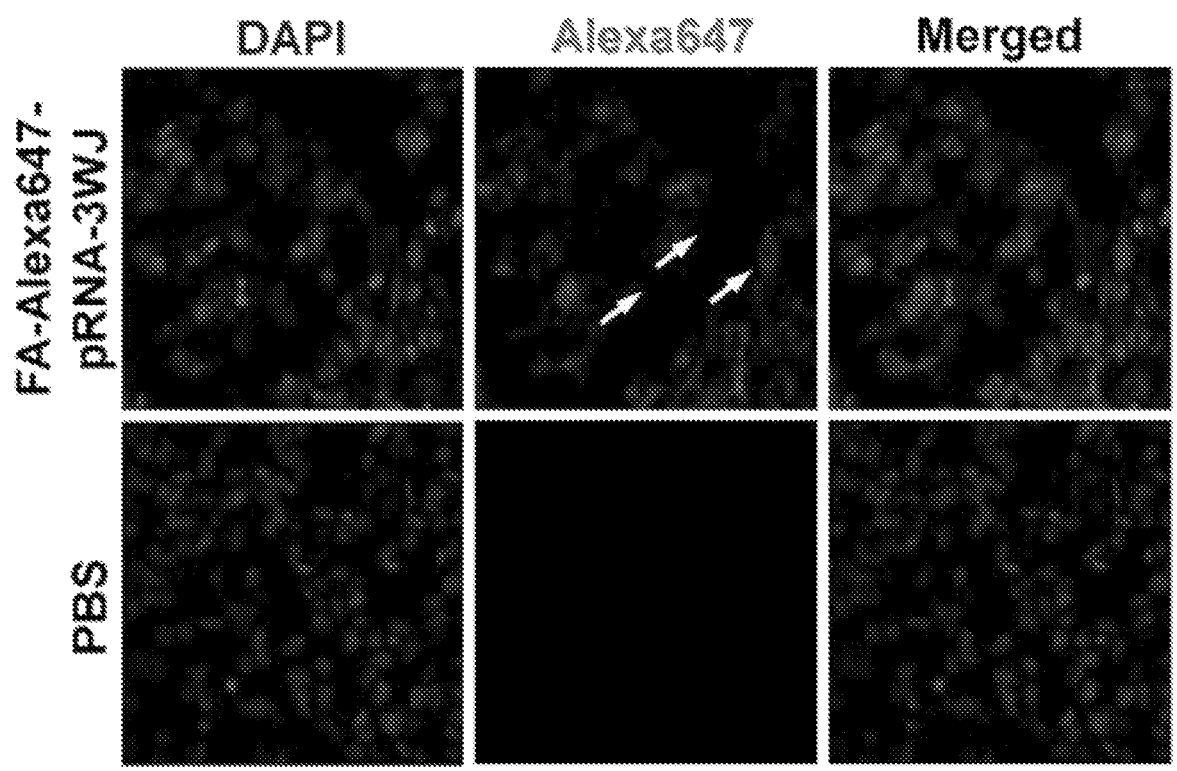
FIG. 7 includes images showing confocal fluorescence imaging of frozen sectioned brain tumor derived from human glioblastoma patient-derived stem cell 1123 demonstrating the distribution and accumulation of FA-Alexa647-pRNA-3WJ RNP in brain tumor cells (yellow arrows). Pseudocolor was used for nuclear (blue), and Alexa647 (red).

Next, we tested whether FA-pRNA-3WJ RNP can specifically target tumor cells in vivo using an orthotropic mouse model of glioblastoma. On the 14th day post U87EGFRvIII cell implantation into nude mouse brain, intracranial tumor growth in mice was determined by MRI (FIG. 2C, top) and randomly separated into three groups for injection of PBS, Alexa647-pRNA-3WJ as two negative controls and FA-Alexa647-pRNA-3WJ as experimental. Each group of mice (n=4) was injected via tail vein (1 mg/kg of RNP in 100 µL of PBS). Fifteen hours post injection, the mice brains were dissected and subjected to fluorescence imaging to detect the Alexa647 signal from RNP. A higher fluorescence signal of Alexa647 was observed in the brains of mice injected with FA-Alexa647-pRNA-3WJ than that in the mice brains injected with control RNP (Alexa647-pRNA-3WJ) (FIG. 2C). ANOVA analysis on the fluorescence intensity from each group (n=4) normalized by their tumor volumes (Alexa647 intensity/tumor volume) confirmed the significant increase in average fluorescence intensity in the mouse brains treated with FA-Alexa647-pRNA-3WJ ($2.052\pm0.416$, s.e.m.) compared to Alexa647-pRNA-3WJ ($1.014\pm0.279$, s.e.m.) ($p=0.019$) with respect to PBS ($1.000\pm0.298$, s.e.m.) (FIG. 2D). The brain tumor region was frozen sectioned (10 µm thick) and further examined under a fluorescence confocal microscope. It revealed that FA-Alexa647-pRNA-3WJ RNP was mostly associated with counterstained brain tumor cells (Supplementary FIG. 7). These in vivo data strongly indicated that systemically injected FA-Alexa647-pRNA-3WJ RNP can travel to brain tissue, and successfully recognize and bind human glioblastoma cells through FA-FR interaction, rather than randomly distribute throughout the entire brain tissues.

Figure 3:
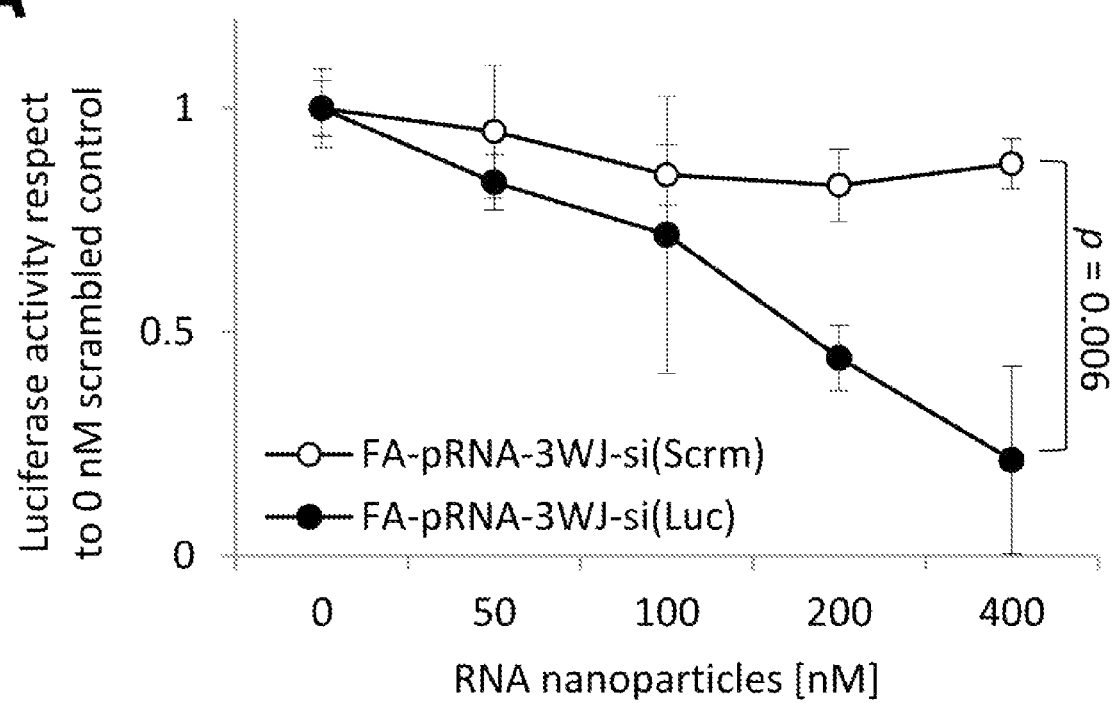
FIG. 3, panels A-E are graphs and images showing gene silencing effect of FA-pRNA-3WJ-si(Luc) RNP in human glioblastoma cells and derived tumor. A, A wide range (up to 400 nM) of FA-pRNA-3WJ-si(Luc) (closed circles) or FA-pRNA-3WJ-si(Scrm) (negative control, open circles) RNPs were incubated with U87EGFRvIII-Luc cells in vitro ($n=4$). The change of luciferase activity was monitored versus the concentration of the RNPs. B, Luciferase gene silencing effect of FA-pRNA-3WJ-si(Luc) in vivo after total of three injections. Luciferase activity change by FA-pRNA-3WJ-si(Luc) (closed circles) or FA-pRNA-3WJ-si(Scrm) (open circles) were compared by mean bioluminescence intensity ($n=5$), $p=0.007$. C, Representative in vivo MRI images for tumor volume and bioluminescence intensity for luciferase activity from both FA-pRNA-3WJ-siRNA(Luc) or FA-pRNA-3WJ-si(Scrm) after three injections. D, Tumor volumes calculated from MRI compared to scrambled control group at day 13 post-xenograft, $p=0.468$ ($n=5$). E, Mean fluorescence intensity divided by tumor volume ($mm^3$) was used to normalize the variation among the tested mice, $p=0.015$ ($n=5$). All error bars indicate s.e.m., and student t-test was used for statistical analysis.
Figure 3:
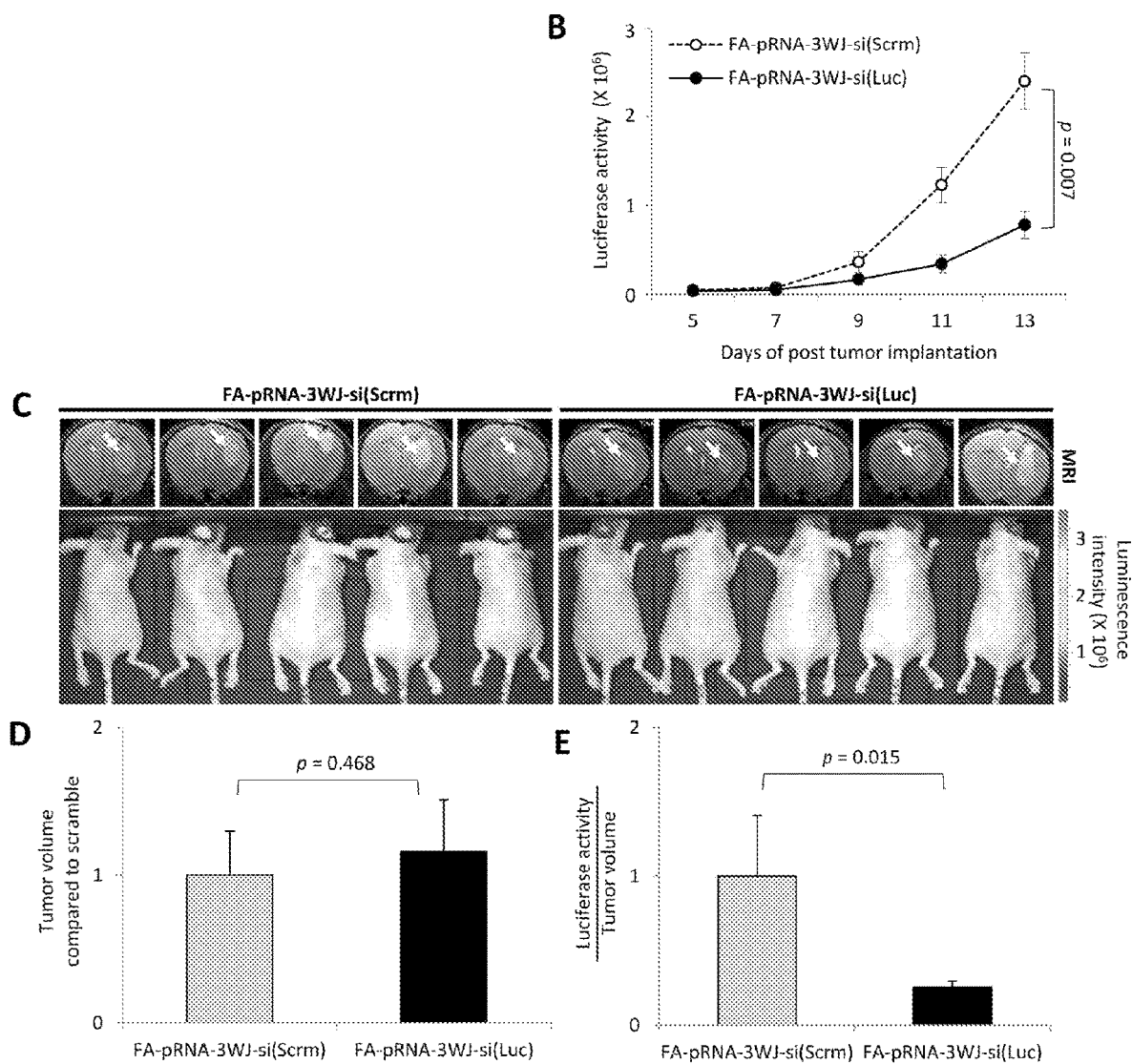
Figure 4:
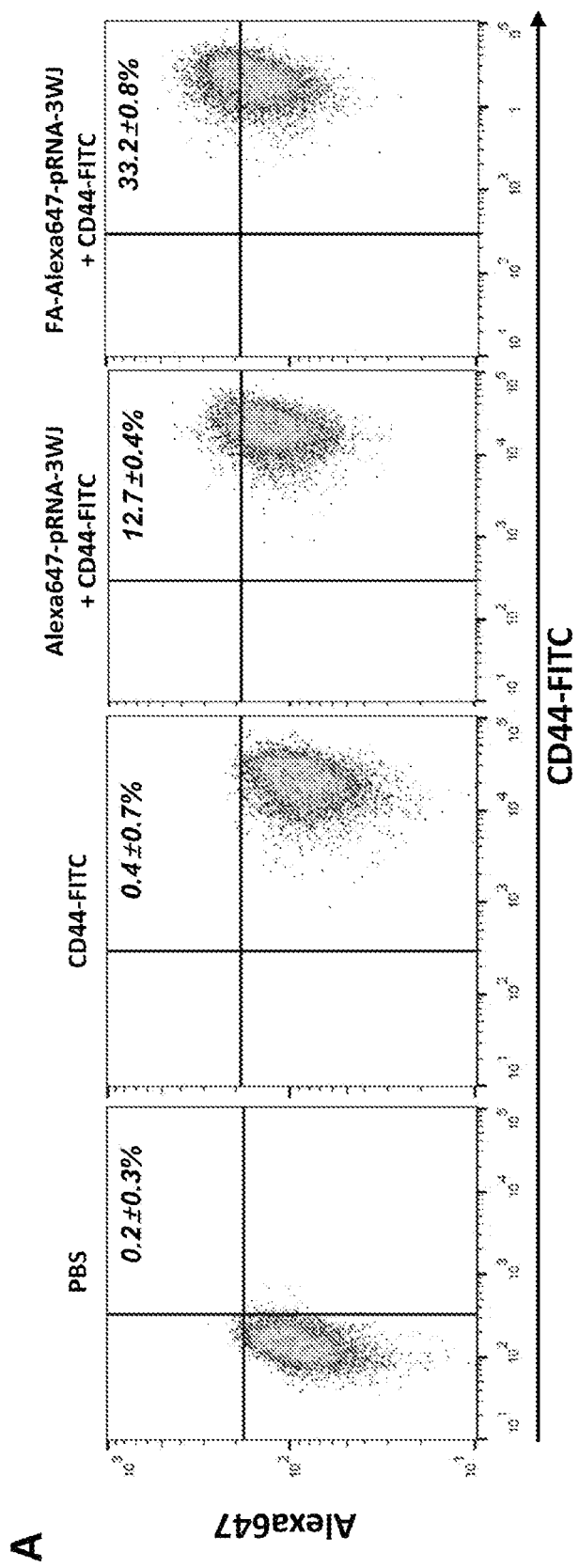
FIG. 4, panels A-C are graphs and images showing FA-mediated targeting of human glioblastoma patient-derived stem cell and derived brain tumor by FA-Alexa647-pRNA-3WJ RNPs in animal trials and biodistribution study. A. Flow cytometry analysis for in vitro targeting of human glioblastoma patient-derived stem cell, 1123, by FA-Alexa647-pRNA-3WJ or Alexa647-pRNA-3WJ RNP co-treated with CD44-FITC antibody. PBS and CD44-FITC treated cells were used as gating controls. B, Mouse brain tumor derived from 1123 cells was evaluated by MRI for tumor size determination (top). After systemic administration of FA-Alexa647-pRNA-3WJ RNP, FA-dependent targeting was visualized by fluorescence in vivo imaging in comparison to FA-free Alexa647-pRNA-3WJ RNP. C, Biodistribution profile of FA-Alexa647-pRNA-3WJ RNP was obtained by imaging fluorescence against Alexa647 from major internal organs collected together with brain.
Figure 4:
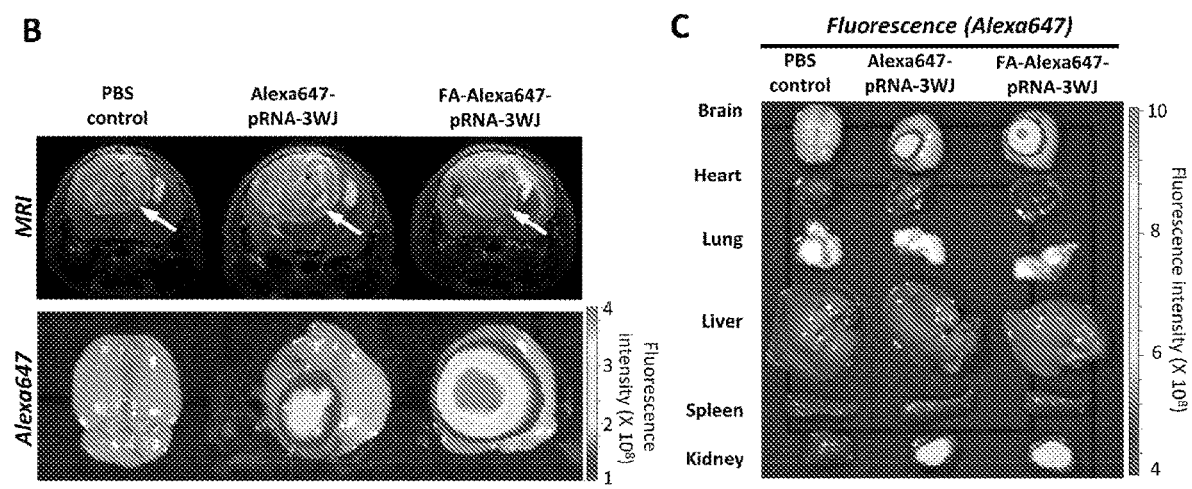

After binding to target glioblastoma cells, RNP needs to internalize to deliver its cargo, siRNA, for successful target gene silencing, which is the most critical property for any nanoparticle to claim its therapeutic application. In order to test whether siRNA-loaded FA-3WJ RNP can silence the target gene in glioblastoma cells in mouse brain after systemic administration, we set up a luciferase-based gene expression reporter system by implanting luciferase gene-expressing U87EGFRvIII cells (U87EGFRvIII-Luc) in mouse brain. For a preliminary in vitro test, U87EGFRvIII-Luc cells were incubated for 72 hrs in culture medium containing a range between 0 and 400 nM of FA-pRNA-3WJ-si(Luc) or scrambled RNA-conjugated control FA-pRNA-3WJ-si(Scrm) RNPs without any transfection agent. After 72 hrs, FA-pRNA-3WJ-si(Luc) clearly reduced luciferase activity in a concentration dependent manner. At 400 nM, average luciferase activity in U87EGFRvIII-Luc cells incubated with FA-pRNA-3WJ-si(Luc) was decreased about five folds ($0.214\pm0.210$, s.e.m.) with respect to 0 nM. However, FA-pRNA-3WJ-si(Scrm) did not significantly reduce luciferase activity in the cells ($0.876\pm0.056$, s.e.m.) compared to 0 nM. The difference of luciferase activity at 400 nM between FA-pRNA-3WJ-si(Luc) and FA-pRNA-3WJ-si(Scrm) was statistically significant ($p=0.006$) (FIG. 3A). For in vivo test, intracranial tumor in mice was induced by implanting U87EGFRvIII-Luc cells. Bioluminescence signal measured from the resulted brain tumor is expected to correlate with tumor growth. When a group of brain tumor-bearing mice (n=5) were systemically injected with FA-pRNA-3WJ-si(Scrm) (1 mg/kg in 100 µL of PBS) for a total of three times over 6 days, the luciferase activity rapidly increased as the tumor grew indicating no effect of the control RNP on luciferase gene expression. However, luciferase activity from the group of mice (n=5) injected with FA-pRNA-3WJ-si(Luc) was observed to increase very slowly over time (FIG. 3B). After 3 injections, the luciferase activity from the mice injected with FA-pRNA-3WJ-si(Luc) was significantly lower ($p=0.007$) than that from the control group mice injected with FA-pRNA-3WJ-si(Scrm). The luciferase activity from the tested mice at day 13 post tumor implantation was mostly lower than that from the mice treated with FA-pRNA-3WJ-si(Scrm) (FIG. 3C). However, MRI revealed that the relative tumor size between those two groups was statistically insignificant ($1.160\pm0.352$ mm$^3$, s.e.m. with respect to $1.000\pm0.300$ mm$^3$ in negative control group) ($p=0.468$, n=5) (FIG. 3D). When their luciferase activity was normalized by the tumor volumes, the relatively averaged luciferase activity over tumor volumes from the mice treated with FA-pRNA-3WJ-si(Luc) ($0.255\pm0.040$ Luminescence Radiance [p/s/cm$^2$/sr]/tumor volume [mm$^3$], s.e.m.) was significantly lower compared to the control mice group treated with FA-pRNA-3WJ-si(Scrm) ($1.000\pm0.410$ Luminescence Radiance [p/s/cm$^2$/sr]/tumor volume [mm$^3$], s.e.m.) ($p=0.015$, n=5) (FIG. 4E). These data strongly indicated that FA-pRNA-3WJ RNP not only specifically targeted glioblastoma cells, but also successfully internalized into the cells and delivered the cargo siRNA. The delivered siRNA, more importantly, remained functionally intact for the whole time of systemic delivery, confirming both stability and therapeutic efficacy of the FA-pRNA-3WJ RNPs. The data successfully demonstrated the therapeutic usability as a siRNA delivery system for glioblastoma treatment.

In clinical settings, glioblastomas are notorious for their frequent recurrence with increased aggressiveness after initial therapy, resulting in poor survival rates. It has been hypothesized that glioblastoma stem cells tend to survive the initial treatment and induce tumor recurrence, meaning that any therapeutic strategy lacking the ability to kill glioblastoma stem cells would not prevent recurrences (23). The potential of FA-pRNA-3WJ RNPs to target glioblastoma stem cells and their derived tumor cells was investigated. We used human glioblastoma patient-derived primary neurosphere cells, named "1123", which has been shown to possess stem cell-like characteristics including a high level of CD44 expression, self-renewal capability and tumorigenicity when implanted in mouse brain (24-26). First, the CD44$^+$ 1123 cells, maintained in serum-free sphere culture medium, were incubated in vitro with 200 nM of either FA-Alexa647-pRNA-3WJ or Alexa647-pRNA-3WJ RNPs. Flow cytometry analysis revealed higher FA-Alexa647-pRNA-3WJ binding to the 1123 cells than control RNP (Alexa647-pRNA-3WJ) (FIG. 4A). Compared to PBS-treated 1123 cells, $33.2\pm0.8\%$ of CD44$^+$ 1123 cells were positively associated with FA-Alexa647-pRNA-3WJ RNP. However, Alexa647-pRNA-3WJ control RNP was associated with only $12.7\pm0.4\%$ of CD44$^+$ 1123 cells. The difference between FA-Alexa647-pRNA-3WJ and Alexa647-pRNA-3WJ was statistically significant ($p<0.0001$).

For systemic assessment, a group of mice was then implanted with 1123 cells to induce intracranial brain tumor. Determined by MRI, mice bearing a similar size of brain tumors were then injected with PBS, Alexa647-pRNA-3WJ or FA-Alexa647-pRNA-3WJ RNPs in 100 µL of PBS through the tail vein. Fifteen hours post injection, the brains were dissected out and subjected to fluorescence imaging.

Figure 8:
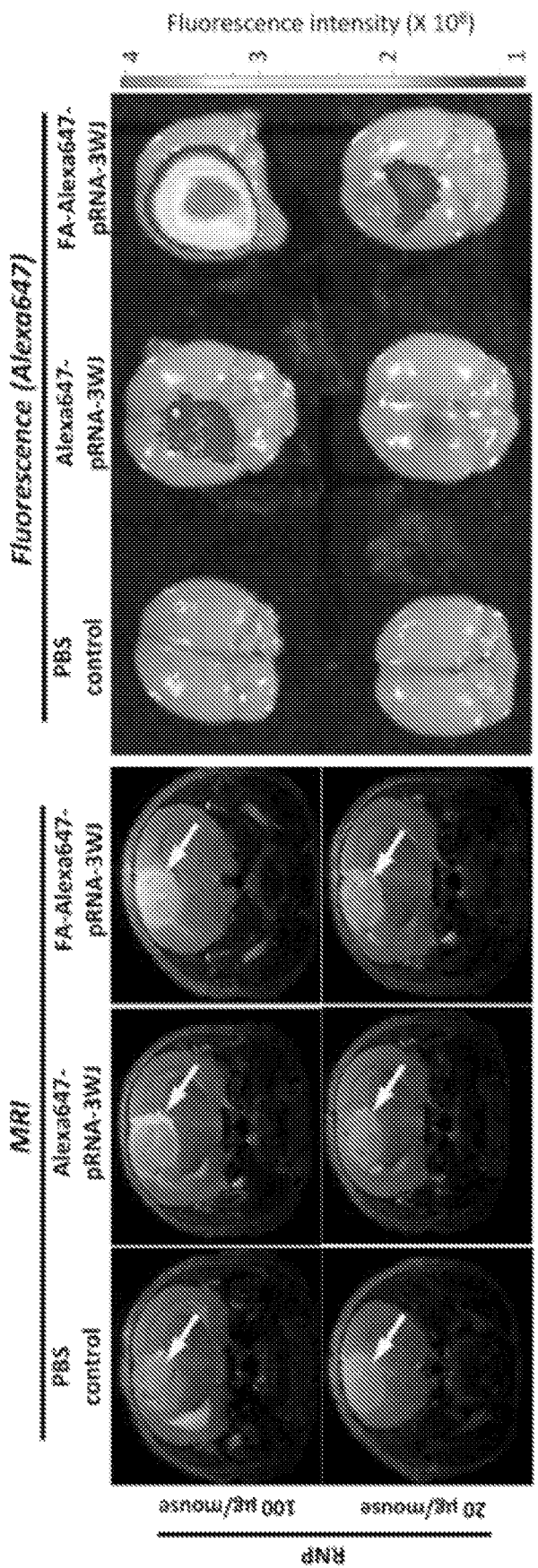
FIG. 8 includes images showing human glioblastoma patient-derived stem cell 1123-derived mouse brain tumor targeting by FA-Alexa647-pRNA-3WJ RNPs with RNA dose-dependent (100>20 µg/mouse) manner. The fluorescence intensity for the tumor-bearing mouse brains were evaluated at 15 hrs after systemic injection of RNPs.

Higher accumulation of FA-Alexa647-pRNA-3WJ RNP was observed in the tumor region, while less accumulation of Alexa647 signal was observed from the brains treated with either control RNP (Alexa647-pRNA-3WJ) or PBS (FIG. 4B). When two different dosages of FA-Alexa647-pRNA-3WJ RNPs (20 or 100 μg/mouse) were tested in a group of mice bearing small sized tumors, fluorescence signals were proportional to the amount of RNPs injected (Supplementary FIG. 8). These observations suggests that FA-Alexa647-pRNA-3WJ RNP can also recognize and target human glioblastoma stem cells and their derived tumor cells through FA-FR specific interaction. Throughout these studies, a fluorescence signal from the groups treated with FA-free 3WJ-pRNA control RNP was also observed although the extents were always lower than the groups treated with FA-3WJ-pRNA RNP. This might be explained by the nature of tumor induced from human patient derived stem cell-like glioblastoma cells, in which the aggressive hypervasculature leaves a large portion of blood vessels as "leaky" as they are poorly finished before forming a tight junction of the BBB, also called the EPR (enhanced permeability and retention) effect (27).

To assess the biodistribution profile of the pRNA-3WJ RNP throughout the body after systemic administration, major internal organs, including heart, lung, liver, spleen and kidney, were also collected together with brain and subjected to fluorescence imaging. Compared to brain, no significant fluorescence signal was detected from the internal organs except kidney (FIG. 4C). The biodistribution profile of FA-pRNA-3WJ RNP after its systemic administration was consistent with the previous report (28), in that FA-conjugated drugs that failed to target tumor cells are rapidly cleared from a mouse body ($t_{1/2}$<10 min) through the kidney, reducing the safety concern of unbound pRNA-3WJ nanoparticles circulating in the blood (7,12-14).

For successful clinical application of pRNA-3WJ RNP for human glioblastoma detection and treatment, it was critical to evaluate its capability to access brain tumor cells by discriminating them from adjacent normal brain cells, and to have favorable biodistribution. To address those two goals, the most critical checkpoints deciding the drugability of the pRNA-3WJ nanoparticles, we employed an orthotropic intracranial glioblastoma model system in mice. According to our observations, it was clear that FA-conjugated FA-pRNA-3WJ RNP can target human glioblastoma cells through FA-FR specific interaction-mediated endocytosis by distinguishing glioma cells from adjacent normal brain cells. A series of in vitro experiments indicated that such targeting in vivo was not obviously a result of non-specific accumulation for two reasons: 1) association of FA-pRNA-3WJ RNP with glioblastoma cells was ligand-dependent; and 2) the association was mediated through FA-FR specific interaction, since free folate pre-treatment interfered with the specific interaction between FA and FRs on the targeted cells. This suggests that FA-pRNA-3WJ RNP can target and accumulate in $FR^+$ glioblastoma cells. Taken together with the fact that our brain imaging data were collected 15 hrs post injection of FA-3WJ RNA nanoparticles and the luciferase gene silencing effect was seen for days, these data suggest that FA-pRNA-3WJ RNP can survive in the body by retaining the chemical integrity of cargo siRNA until it reaches the brain. Most importantly, the therapeutic delivery by the FA-3WJ RNA nanoparticles was clearly demonstrated by targeting endogenous luciferase mRNAs as a reporter system (FIG. 3). The decreased luciferase activity observed from a group of mice injected with FA-3WJ-pRNA-si(Luc) RNP clearly answered questions towards the capability of the FA-3WJ RNP regarding: 1) specific targeting to brain tumor cells; 2) internalization into brain tumor cells; and 3) releasing the functional moiety (siRNA against luciferase mRNA). In addition, the targeting capability of pRNA-3WJ nanoparticles for both brain tumor cells and glioblastoma stem cells through a FA-FR mediated manner will overcome the weak point of conventional brain tumor therapies which largely relies on surgical debulking and less-specific toxic drugs with radiation. In summary, our current study successfully demonstrated the drugability of FA-conjugated pRNA-3WJ RNP as therapeutic gene delivery for clinical applications to meet the urgent need of new strategies to target and kill both glioblastoma stem cells and their derived tumor cells. Due to the ease and flexibility of modification of each RNA module, any drug conjugation and siRNA can be loaded to the RNP as therapeutic functionalities. Recently, microRNAs have been found to involve in pathological process in glioblastoma making them as promising therapeutic targets (29-32). Since size and working mechanism of miRNAs are similar to those of siRNAs (21), therapeutic miRNAs also can be considered to be loaded onto the pRNA-3WJ-RNP.

Methods

Construction of FA-Alexa647-pRNA-3WJ-si(Luc) RNP

Multifunctional pRNA-3WJ RNP was prepared as previously described (7, 12, 13, 22) with slight modifications. In brief, three RNA modules, named $a_{3WJ}$(5'-UUGCCAUGU-GUAUGUGG-3' (SEQ ID NO: 1)), $b_{3WJ}$(5'-CCCA-CAUACUUUGUUGAUCC-3' (SEQ ID NO: 2)), and $c_{3WJ}$ (5'-GGAUCAAUCAUGGCAA-3' (SEQ ID NO: 3)), were transcribed in vitro or synthesized chemically using 2'-F modified nucleotides and purified separately to homogeneity. For the current study, each RNA module was further modified as following: module $a_{3WJ}$ was extended with luciferase siRNA sequences sense: 5'-CUUACGCUG-AGUACUUCGAUU-3' (SEQ ID NO: 4) and anti-sense: 5'-UCGAAGUACUCAGCGUAAGUU-3' (SEQ ID NO: 5), or scrambled as negative control; module $b_{3WJ}$ was conjugated with FA at the 3' end; and module $c_{3WJ}$ was conjugated with fluorophore Alexa647 (Alexa Fluor® 647, Invitrogen) at the 3' end. The three RNA modules were mixed at equal molar ratio to form one-step self-assembly. The self-assembled FA-Alexa647-pRNA-3WJ-si(Luc) RNPs were purified from 6 M urea-containing PAGE and frozen at −80° C. after reconstituted in PBS. To obtain the designated concentration for each experiment, the RNPs were further diluted in PBS before use.

Characterization of Self-Assembled FA-Alexa647-pRNA-3WJ-si(Luc) RNP

Three dimensional structure and shape of the final form of self-assembled FA-Alexa647-pRNA-3WJ-si(Luc) RNP was analyzed by atomic force microscopy (AFM) imaging as described previously.[7,12,13,22] Apparent hydrodynamic sizes and zeta potential of pre-assembled FA-Alexa647-pRNA-3WJ-si(Luc) RNP (1.5 μM) in PBS buffer was measured by Zetasizer nano-ZS (Malvern Instrument) at 25° C. The laser wavelength was 633 nm. The data were obtained from three independent measurements.

Human Glioblastoma Cells and Human Patient-Derived Glioblastoma Stem Cells

Human glioblastoma cells, U87EGFRvIII and U87EGFRvIII-Luc (expressing luciferase reporter gene), were obtained from Dr. Webster Cavenee (Ludwig Cancer Institute, San Diego, Calif.). Both cells were maintained in DMEM/10% FBS/penicillin/streptomycin. Human glioblastoma patient-derived glioblastoma stem cell "1123" was cultured in DMEM/F12 (Invitrogen) supplemented with B27 (1:50), heparin (5 mg/mL), basic FGF (bFGF) (20 ng/mL), and EGF (20 ng/mL). Growth factors (bFGF and EGF) were added twice a week (24).

Intracranial Human Glioblastoma Xenografts from Human Glioblastoma Cells and Human Patient-Derived Glioblastoma Stem Cells Six weeks old athymic female nu/nu mice (Jackson Laboratory, Bar Harbor, Me.) were housed and handled in accordance with the Subcommittee on Research Animal Care of the Ohio State University guidelines approved by the Institutional Review Board. All mice were fed folate-free diet (Harlan, Indianapolis, Ind.) for at least two weeks before tumor implantation. Intracranial human glioblastoma xenograft tumor was induced by implanting human glioblastoma cell U87EGFRvIII or human patient-derived glioblastoma stem cells ($1\times10^5$ cells per mouse), as described previously (33). Two weeks post intracranial tumor implantation, the location and size of the implanted tumors were determined by magnetic resonance imaging (MM).

Magnetic Resonance Imaging (MRI) for Location and Size of Implanted Brain Tumor in Mice On the indicated day post-surgery of intracranial tumor injection, the location and size of the implanted tumors were determined by magnetic resonance imaging (MRI). Mouse was anesthetized with 2.5% isoflurane mixed with 1 L/min carbogen (95% $O_2$ with 5% $CO_2$), then maintained with 1% isoflurane thereafter. Maintaining core temperature using a warm water bath, imaging was performed using a Bruker Biospin 94/30 magnet (Bruker Biospin, Karlsruhe, Germany). Mice were injected with Magnevist, gadolinium-based contrast agent (Bayer Health Care Pharmaceuticals, Wayne, N.J.) by an i.p. administration with 0.5 mmol/kg dose, then positioned in the magnet. T2-weighted RARE imaging was collected using a sequence (TR=3524 ms, TE=36 ms, rare factor=8, navgs=2, FOV=20×20 mm, 0.5 mm slice thickness). Region-of-interest (ROI) was manually outlined based on contrast in signal intensity between brain and tumor tissue.

Fluorescence Confocal Microscopy for In Vitro and In Vivo RNP Binding

For the in vitro targeting test of pRNA-3WJ RNP, $2\times10^3$ of U87EGFRvIII (malignant human glioblastoma) cells in 200 µL were plated in Lab-TekII 8-well chamber slide (Nunc, Rochester, N.Y.). The next day, the cells were washed with PBS and incubated with 200 nM of either FA-Alexa647-pRNA-3WJ RNP or control RNP (Alexa647-pRNA-3WJ) in 200 µL of culture media for 2 hrs at 37° C. in a $CO_2$ incubator. To block cellular FRs by free folate, PBS-washed cells were pre-treated with 1 mM free folate in 200 µL of culture media for 1 hr at 37° C. in a $CO_2$ incubator before RNP treatment. After washing with PBS, the RNP-treated cells were fixed in 4% paraformaldehyde (PFA) solution for 2 hrs at 4° C. The cytoskeleton of the fixed cells was stained by Alexa Fluor 488 Phalloidin (Invitrogen, Grand Island, N.Y.) for 30 min at room temperature and the nucleus stained with 0.01% DAPI solution for 10 min at room temperature. The cells were then rinsed with PBS for 3×10 min and mounted with PermaFluor Aqueous Mounting Medium (Thermo Scientific). Fluorescence microscopy was performed using Olympus 4-filter-based FluoView FV1000-Filter Confocal Microscope System (Olympus Corp.) at the wavelengths of 461 nm (for the cell nucleus stained by DAPI), 530 nm (for the cytoskeleton stained by Alexa Fluor 488 Phalloidin) and 665 nm (for the Alexa647). Images were analyzed by Olympus FluoView Viewer software ver. 4.0 (Olympus). For in vivo targeting, the brain tumor xenograft collected 15 hrs after RNP injection was fixed in 4% PFA with 10% sucrose in PBS overnight at 4° C. and embedded in Tissue-Tek® O.C.T. compound (Sakura Finetek USA, Inc., Torrance, Calif.) for frozen sectioning (10 µm thick). The sectioned samples were mounted by ProLong® Gold Antifade Reagent with DAPI (Life Technologies Corporation, Carlsbad, Calif.) overnight. The fluorescent images were obtained using FluoView FV1000-Filter Confocal Microscope System (Olympus Corp.).

Flow Cytometry for In Vitro RNP Binding

Flow cytometry analysis was performed for in vitro targeting by pRNA-3WJ RNP in malignant human glioblastoma (U87EGFRvIII) and glioblastoma stem cells (1123). The cells were plated in 6-well plate one day before RNP binding. After washing with PBS, the cells were incubated with 200 nM of either FA-Alexa647-pRNA-3WJ RNP or Alexa647-pRNA-3WJ RNP in 200 µL of culture media for 2 hrs at 37° C. in a $CO_2$ incubator. For blocking cellular FRs by free folate, the PBS-washed cells were pre-treated with 1 mM of free folate in 200 µL of culture media for 1 hr in 37° C. $CO_2$ incubator before RNP treatment. After washing with PBS, the cells were harvested by trypsinization and fixed in 4% PFA solution for 2 hrs at 4° C. The cells were washed with PBS for 3 times at room temperature, then subjected to Flow Cytometry analysis using BD FACS Aria-III Cell Sorter. The data were analyzed by FlowJo 7.6.1 software.

Systemic Injection of RNPs to Intracranial Human Glioblastoma Xenograft Tumor Bearing Mice Based on the MRI evaluation taken one day before RNP injection, a group of mice bearing similarly sized tumors at similar location was selected for systemic injection of RNPs. Designated amount of RNPs (1 mg/kg of mouse body weight) prepared in 100 µL of PBS were injected through mouse tail vein. After 15 hrs of RNP injection, the brains were dissected out and subjected to fluorescence imaging. Tumor volume calculated from MRI was also used to normalize fluorescence intensity or luciferase activity for each mouse as described below.

Fluorescence Imaging on Human Glioblastoma Xenograft Mouse Brain Tumor

To investigate the delivery of pRNA-3WJ RNPs in vivo, a brain fluorescence imaging study was performed after tail vein injection into mice bearing brain tumor. The mice were sacrificed by cervical dislocation under anesthesia 15 hrs post injection, and brains were dissected out of mice. Fluorescence signals were detected from the dissected brains using IVIS Lumina Series III Pre-clinical In Vivo Imaging System (Perkin Elmer, Waltham, Mass.) with excitation at 640 nm and emission at 660 nm for 2 min exposure. The fluorescence intensity was expressed as Mean Radiant Efficiency $[p/s/cm^2/sr]/[\mu W/cm^2]$, then normalized by tumor volume ($mm^3$). PBS injected mice were used as fluorescence negative control. Major internal organs together with brain from the harvested mice were collected and subjected to fluorescence imaging for assessment of biodistribution profile study.

Bioluminescence Whole Body Imaging for Luciferase Activity

To investigate the siRNA delivery and silencing effect of pRNA-3WJ RNPs in vivo, U87EGFRvIII-Luc cell-induced brain tumor was prepared into two groups of mice (n=5). At 5, 7 and 9 days post-surgery, 1 mg/kg of mouse body weight of FA-Alexa647-pRNA-3WJ-si(Luc) RNP (or siScrm as negative control) was injected through the mouse tail vein in 100 µL of PBS. After each injection, mice were subjected to bioluminescence whole body imaging to detect the endogenous luciferase expression level. Mice were injected with 75 mg/kg Luciferin (Perkin Elmer, Waltham, Mass.), and anesthetized. Bioluminescence from the anesthetized mice was detected by ZFOV-24 zoom lens-installed IVIS Lumina Series III Pre-clinical In Vivo Imaging System (Perkin Elmer, Waltham, Mass.). The luminescence intensity was expressed as Averaged Radiance [p/s/cm$^2$/sr], then normalized by tumor volume (mm$^3$).

Statistical Analysis

All statistical analyses comparing groups of mice treated with test and control RNPs were performed by either ANOVA or student t-test. p<0.05 was considered significant.

Example 2

Figure 9A:
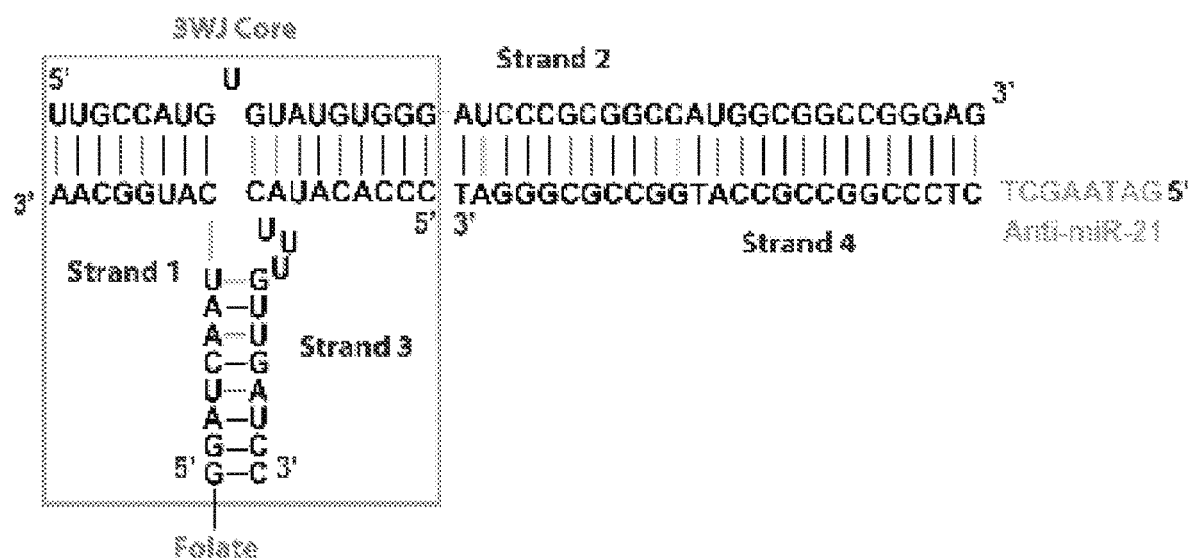
FIG. 9A is a diagram illustrating the construction map of trivalent FA-3WJ-LNA-miR21. Panel A discloses SEQ ID NOS 6, 3, 2 and 7, respectively, in order of appearance.
Figure 9B:
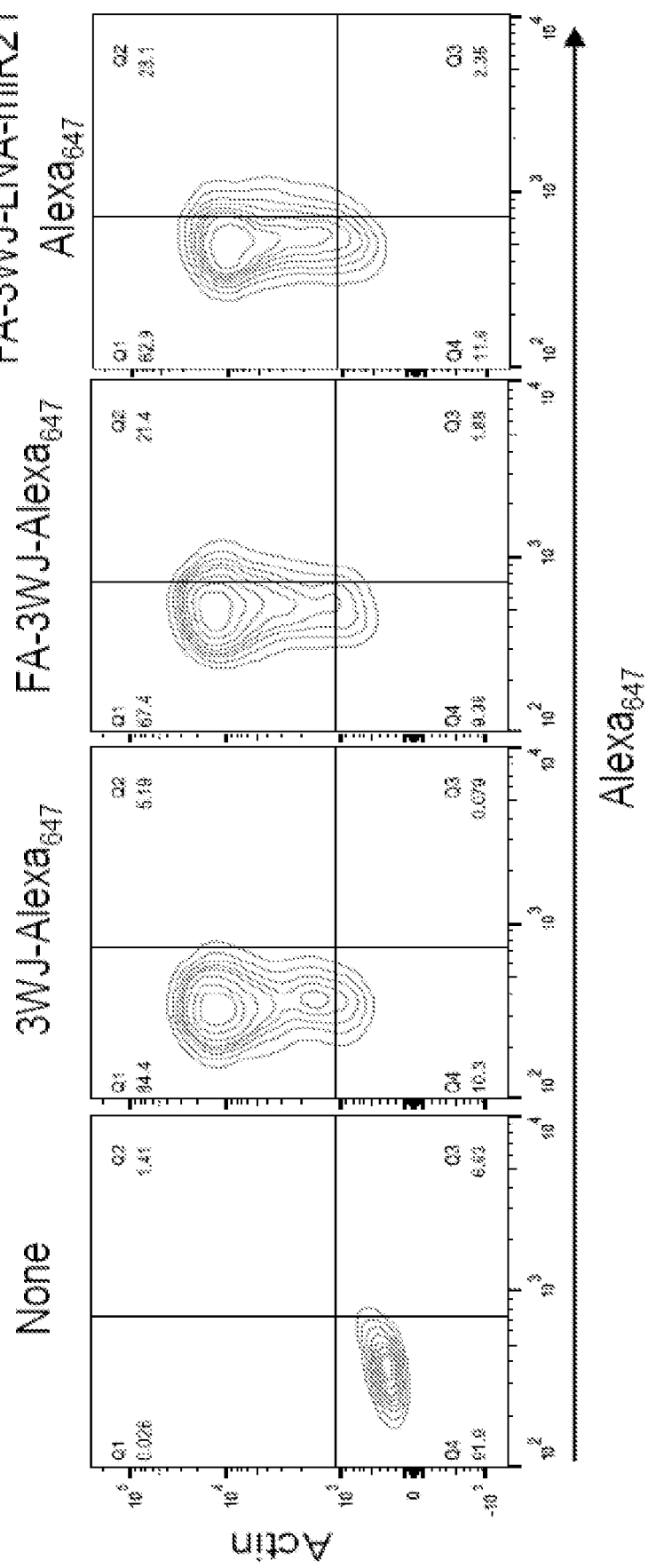
FIG. 9B includes graphs illustrating FA-mediated in vitro human glioblastoma cell targeting determined by flow cytometry.

This study is to determine the specific recognition and binding capability of FA-3WJ-LNA-anti-miR21 RNA nanoparticles (RNP) towards human glioblastoma cells (FIG. 9A), firstly FA-specific association between FA-3WJ-LNA-miR21 conjugated with Alexa647 fluorescent dye and human patient-derived glioblastoma cell GBM30 was assessed in vitro (FIG. 9B). The nanoparticle contains a stand of (SEQ ID NO: 7)
5'-+G+A+T+A+A+G+C+T CTC CCG GCC GCC ATG GCC GCG GGA T-3'

(underlined sequence is 8-mer anti-miR21 LNA).

The cells plated in 6-well plate one day before RNP binding were washed with PBS and incubated with 200 nM of FA-3WJ-LNA-miR21-Alexa647 RNP for 2 hrs at 37° C. in a CO2 incubator. After three times of washing with PBS, the cells were harvested by trypsinization and fixed in 4% PFA solution for 2 hrs at 4° C. and subjected to Flow Cytometry analysis using BD FACS Aria-III Cell Sorter. The cells were identified by staining actin filaments with Phalloidin-Alexa488. Comparison to FA-free control RNP (3WJ-Alexa647), flow cytometry analysis showed a higher association in FA-3WJ-LNA-miR21-Alexa647 (23.1%) (student t-test, p<0.001, n=3). Extra moiety of LNA-miR21 did not affect the specific binding to the GBM30 cells, since FA-3WJ-Alexa647 RNP showed similar level of association (21.4%) to the FA-3WJ-LNA-miR21-Alexa647 (23.1%).

Example 3

Figure 10:
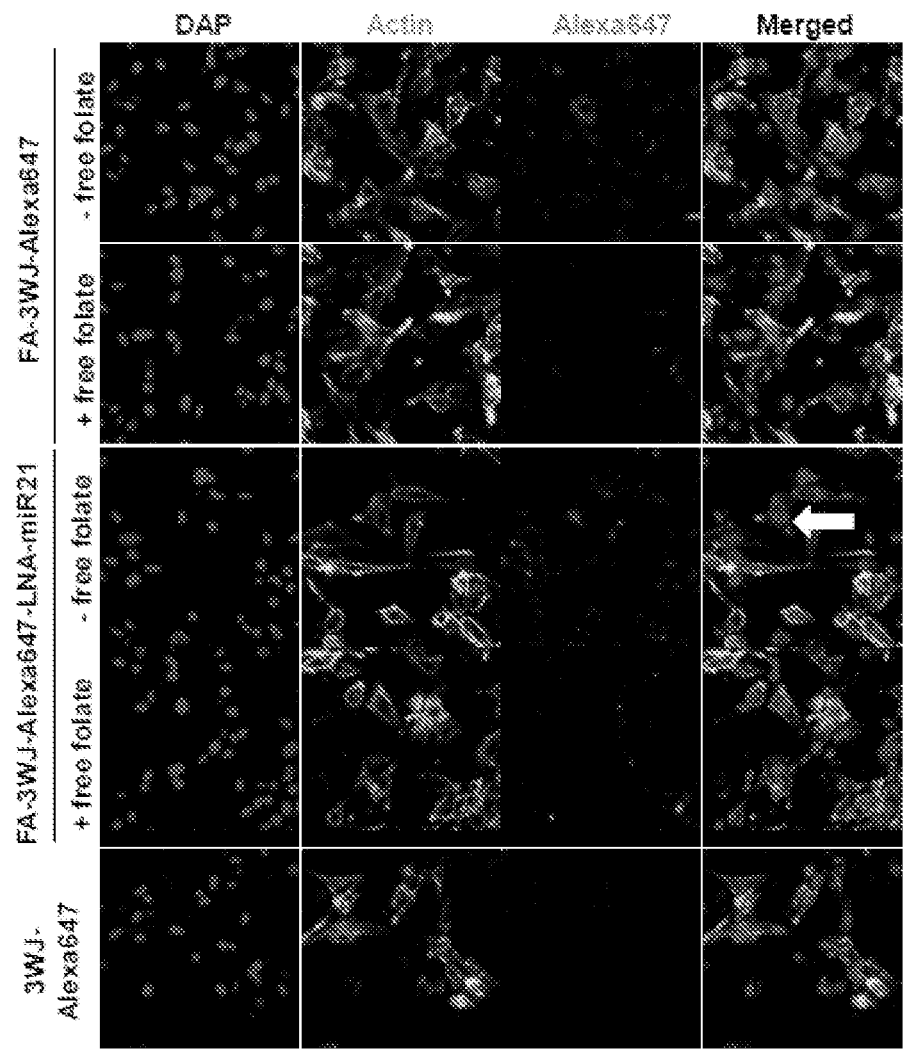
FIG. 10 includes images showing FR-dependent human glioblastoma cell targeting visualized by confocal fluorescent microscopy.

In this study, the folate receptor (FR)-dependent specific binding of FA-3WJ-LNA-miR21-Alexa647 RNP to GBM30 cells was further confirmed by visualizing the Alexa647 signal from surface-cultured GBM30 cells treated with FA-3WJ-LNA-miR21-Alexa647 RNP under confocal fluorescence microscope (FIG. 10). For the in vitro targeting test of FA-3WJ-LNA-miR21-Alexa647 RNP, 2×103 of GBM30 cells in 200 μL were plated in Lab-Tek II 8-well chamber slide. The next day, the cells were washed with PBS and incubated with 200 nM of either FA-3WJ-LNA-miR21-Alexa647 RNP or control RNP (3WJ-Alexa647) in 200 μL of culture media for 2 hrs at 37° C. in a CO2 incubator. The cytoskeleton of the fixed cells was stained by Alexa Fluor 488 Phalloidin (Invitrogen, Grand Island, N.Y.) for 30 min at room temperature and the nucleus stained with 0.01% DAPI solution for 10 min at room temperature. The cells were then rinsed with PBS for 3×10 min and mounted with PermaFluor Aqueous Mounting Medium (Thermo Scientific). Fluorescence microscopy was performed using Olympus 4-filter-based FluoView FV1000-Filter Confocal Microscope System (Olympus Corp.). Higher fluorescence intensity of Alexa647 dye was observed from GBM30 cells treated with FA-3WJ-LNA-miR21-Alexa647 RNP than those with control RNP (3WJ-Alexa647) lacking FA. Again, the FA-dependent association was not affected by the presence of LNA-miR21 sequences, since the FA-3WJ-LNA-miR21-Alexa647 RNP showed comparable association with 3WJ-Alexa647. When FRs of GBM30 cells were premasked by incubating with 1 mM free-folate for 1 hr of culture before the RNP treatment, the association between FA-3WJ-LNA-miR21-Alexa647 RNP and GBM30 cells was abolished to an extent similar to the negative control 3WJ-Alexa647 RNP. Taken together with data shown in FIG. 9, it indicated that the association between FA-3WJ-LNA-miR21-Alexa647 RNP and GBM30 cells was FR dependent medicated by the FA conjugated to the RNP. Yellow arrow indicates the specific localization of FA-3WJ-LNA-miR21-Alexa647 RNP in GBM30 cells, which is presented with magnified view in FIG. 11.

Example 4

Figure 11:
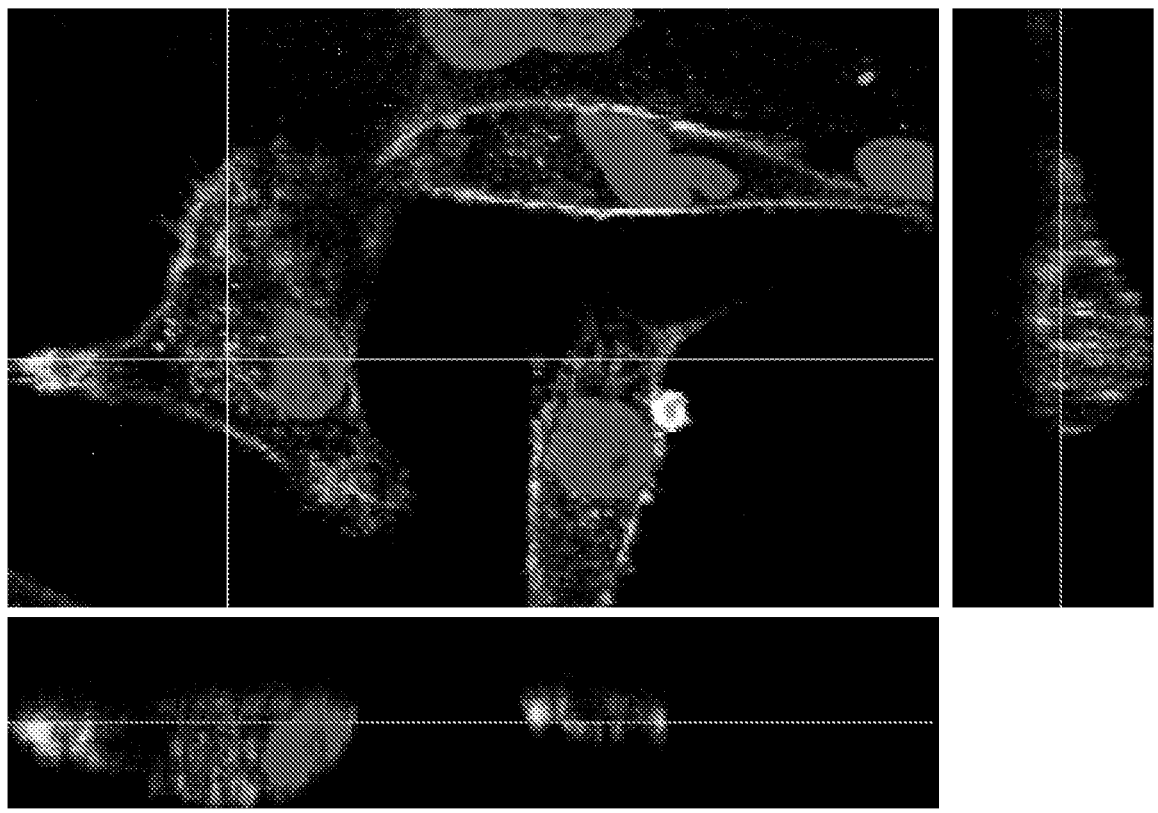
FIG. 11 includes images showing confocal fluorescent microscopy analysis visualizes human glioblastoma cell specific distribution.

This study shows the distribution of FA-3WJ-LNA-miR21-Alexa647 RNP in GBM30 cells after 2 hrs of incubation was visualized by confocal fluorescent microscopy (FIG. 11). The image shows successful internalization of FA-3WJ-LNA-miR21-Alexa647 RNP into GBM30 cells and accumulation in cytoplasm not much in nucleus. Since LNA-miR21 will work against mature miR-21 in cytoplasm to show its small RNA interfering activity, the cytoplasmic distribution of FA-3WJ-LNA-miR21-Alexa647 RNP promises the drugability in target therapy of glioblastoma. Alexa647 was expressed in red peudocolor. The cytoskeleton of the fixed cells was stained by Alexa Fluor 488 Phalloidin (Invitrogen, Grand Island, N.Y.) and the nucleus stained with 0.01% DAPI solution. Fluorescence microscopy was performed using Olympus 4-filter-based FluoView FV1000-Filter Confocal Microscope System (Olympus Corp.) at the wavelengths of 461 nm (for the cell nucleus stained by DAPI), 530 nm (for the cytoskeleton stained by Alexa Fluor 488 Phalloidin) and 665 nm (for the Alexa647). Images were analyzed by Olympus FluoView Viewer software ver. 4.0 (Olympus). The fluorescent images were obtained using FluoView FV1000-Filter Confocal Microscope System (Olympus Corp.).

Example 5

Figure 12:
FIG. 12 includes graphs and images showing anti-tumor effect of systemically delivered FA-3WJ-LNA-miR21 RNP in human glioblastoma cells derived tumor in vivo.
Figure 12:
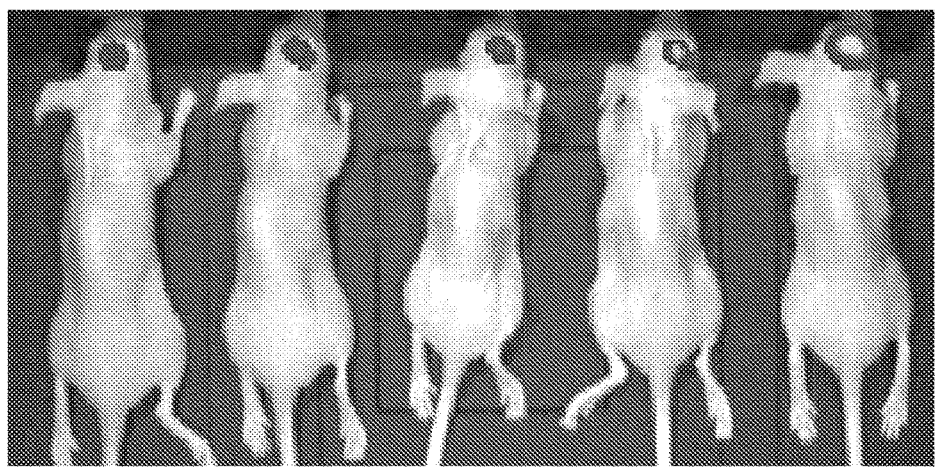
Figure 12:
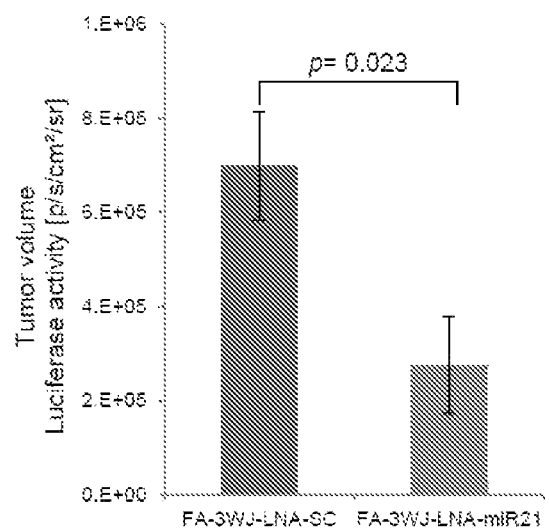

This study shows anti-tumor effect of systemically delivered FA-3WJ-LNA-miR21 RNP in human glioblastoma cells derived tumor in vivo (FIG. 12). For in vivo test, intracranial tumor in mice was induced by implanting GBM-Luc cells expressing luciferase gene which enables the tracing of tumor size change. Bioluminescence signal measured from the resulted brain tumor is expected to correlate with tumor growth. To establish in vivo mouse model, GBM30-Luc cells—induced brain tumor was prepared into two groups of mice (n=5). At 14 days post-surgery, 1 mg/kg of mouse body weight of FA-3WJ-LNA-miR21 RNP (or FA-3WJ-LNA-SC as negative control) was injected through the mouse tail vein in 100 μL of PBS for total of five times. After each injection, mice were subjected to bioluminescence whole body imaging to detect the endogenous luciferase expression level. Mice were injected with 75 mg/kg Luciferin (Perkin Elmer, Waltham, Mass.), and anesthetized. Bioluminescence from the anesthetized mice was detected by ZFOV-24 zoom lens-installed IVIS Lumina Series III Pre-clinical In Vivo Imaging System (Perkin Elmer, Waltham, Mass.). The luminescence intensity was expressed as Averaged Radiance [p/s/cm$^2$;/sr]. When a group of brain tumor-bearing mice (n=5) were systemically injected with FA-3WJ-LNA-miR21 (1 mg/kg in 100 µL of PBS) for five times over 10 days, the luciferase activity rapidly decreased compared to the mice group injected with FA-3WJ-LNA-SC control RNP, indicating the anti-tumor effect of FA-3WJ-LNA-miR21. as the tumor grew indicating no effect of the control RNP on luciferase gene expression. FIG. 12A shows representative in vivo MRI images for tumor volume and bioluminescence intensity for luciferase activity from both FA-3WJ-LNA-miR21 or FA-3WJ-LNA-SC after five injections. FIG. 12B shows tumor volumes calculated from mean fluorescence intensity compared to scrambled control group after five injections, p=0.023 (n=5).

Example 6

Figure 13:
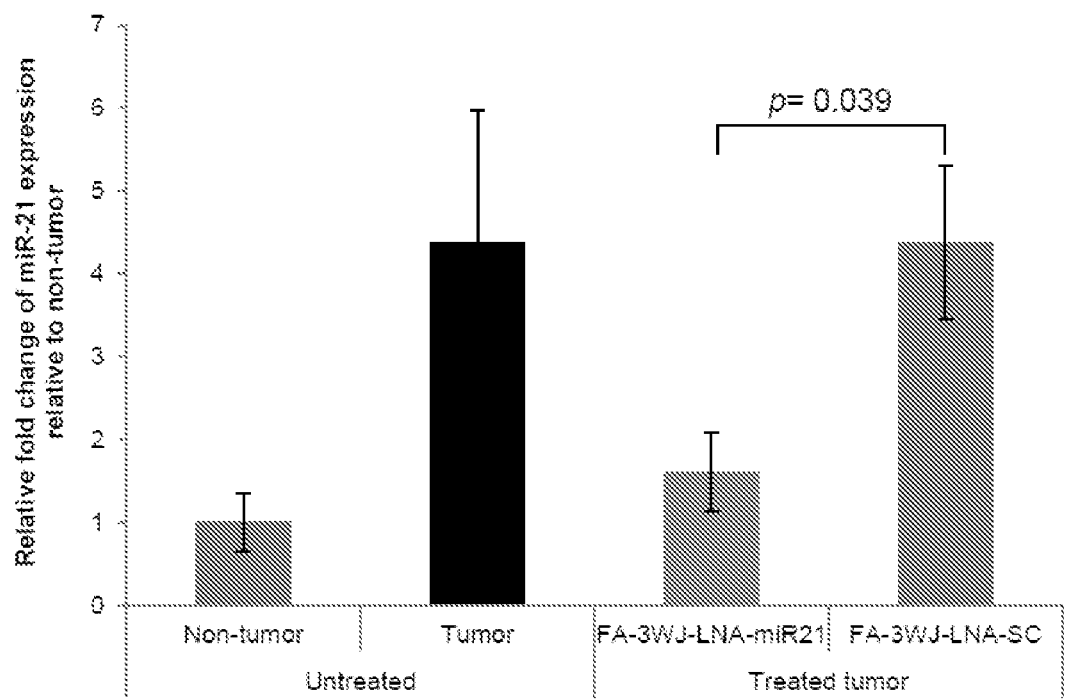
FIG. 13 is a graph illustrating knock-down of endogenous miR-21 in mouse tumor by systemically delivered FA-3WJ-LNA-miR21.

This study shows the Knock-down of endogenous miR-21 in mouse tumor by systemically delivered FA-3WJ-LNA-miR21 (FIG. 13). In this study, LNA-miR21 sequences conjugated to FA-3WJ-LNA-miR21 RNP is expected to silence endogenous miR-21 in mouse tumor induced by GBM30 cells. After five times of systemic administration of FA-3WJ-LNA-miR21 RNP, the tumor was dissected out of mouse brain. Total RNA was extracted from the tumor tissue with Trizol reagent according to the manufacture's protocol. The expression level of miR-21 was determined by TaqMan MicroRNA expression Reverse-transcription analysis kit. snoRNA U6 was used as normalization internal control. Non-tumor brains serve to show endogenous level of miR-21 in normal brain cells. GBM30 cells-induced tumor regions showed relatively higher expression of miR-21 compared to non-tumor region. When the mouse tumors were systemically treated with FA-3WJ-LNA-miR21 RNP, the level of miR-21 in the mouse tumors significantly decreased at least more than two times than the mouse tumors injected with negative control RNP, FA-3WJ-LNA-SC. It critically demonstrated the anti-miR-21 silencing activity of FA-3WJ-LNA-miR21 RNP in vivo mouse models after systemic administration.

Example 7

Figure 14:
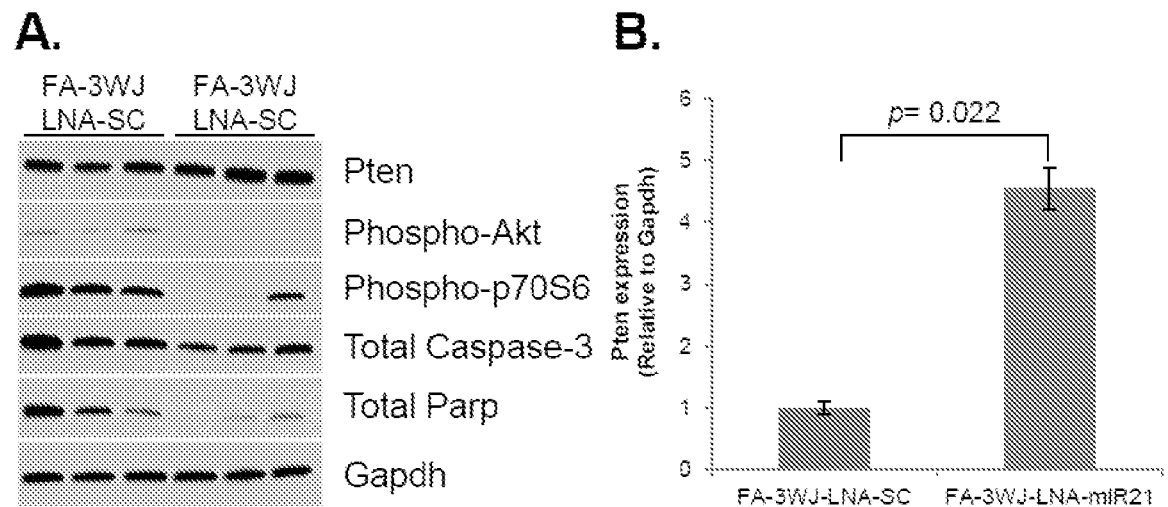
FIG. 14, panels A and B are graphs and images showing down regulation of miR-21 by systemically delivered FA-3WJ-LNA-miR21 induced apoptotic pathway through recovery of Pten protein expression.

This study shows the regulation of miR-21 by systemically delivered FA-3WJ-LNA-miR21 induced apoptotic pathway through recovery of Pten protein expression (FIG. 14). In this study, Pten expression has been reported to be down regulated in glioblastoma, and identified previously as a primary silencing target of over-expressed miR-21 in glioblastoma. Data in FIG. 14 successfully demonstrated the anti-miR-21 silencing effect of to FA-3WJ-LNA-miR21 RNP. To evaluate the miR-21 silencing effect in the down stream miR-21 targets, western blotting analysis was performed on total proteins extracted from mouse tumors after systemically injection of FA-3WJ-LNA-miR21 RNP. FIG. 14A refers to Western blotting identified up-regulation of Pten protein expression in the mouse tumor treated with to FA-3WJ-LNA-miR21 RNP. The increased Pten expression resulted suppression of Akt activity, a primary down stream target of Pten pathway, which activated apoptosis pathway. Evidently, the rescue of Pten expression resulted apoptosis in tumor cells to tumor regression as observed in FIG. 12. The image data in this study was analyzed by ImageJ software. Pten expression was increased at least more than four times in the mouse tumors treated with to FA-3WJ-LNA-miR21 RNP compared to those with to FA-3WJ-LNA-SC RNP (p=0.022, n=5).

Example 8

Figure 15:
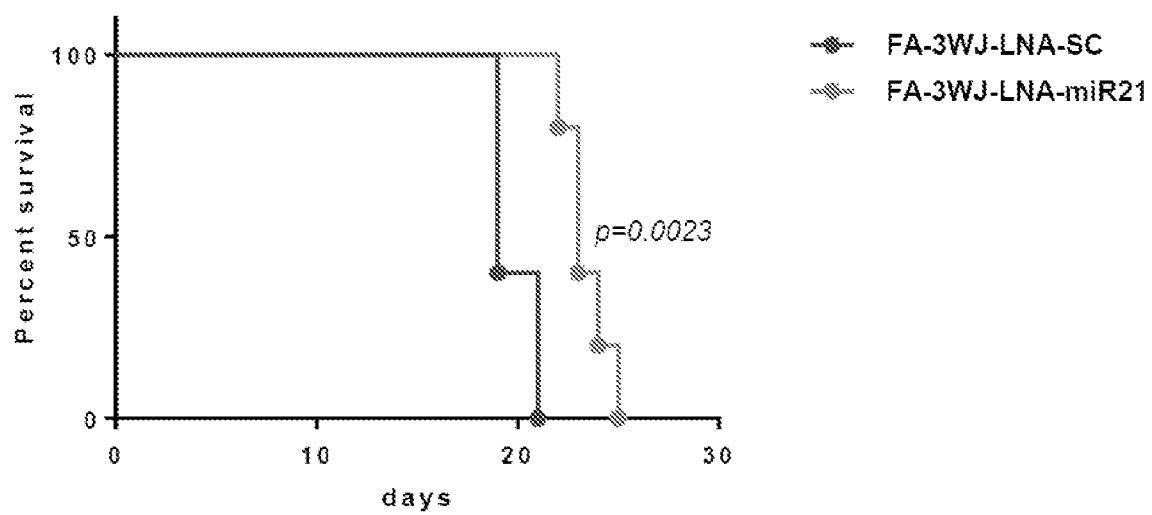
FIG. 15 is a graph showing knock-down of endogenous miR-21 in mouse tumor by systemically delivered FA-3WJ-LNA-miR21 improved overall survival of brain tumor-bearing mice.

This study shows knock-down of endogenous miR-21 in mouse tumor by systemically delivered FA-3WJ-LNA-miR21 improved overall survival of brain tumor-bearing mice (FIG. 15). In this study, Kaplan-Meyer survival curve was used to compare overall survival rates of two brain tumor-bearing mice groups treated with to FA-3WJ-LNA-miR21 RNP and negative control RNP (to FA-3WJ-LNA-SC) after total of five time systemic administrations. As shown above data, apoptosis in mouse brain tumor region activated by the systemically injected FA-3WJ-LNA-miR21 RNP significantly improved the survival rate (p=0.0023, n=5). Median survival rate of the FA-3WJ-LNA-miR21 RNP treated mice group was 23 days, while the mice group treated with FA-3WJ-LNA-SC RNP showed 19 days of median survival rate.

Throughout this document, various references are mentioned. All such references are incorporated herein by reference, including the references set forth in the following list:

REFERENCES

1. Lesniak, M. S.; Brem, H. Targeted Therapy For Brain Tumours. *Nat. Rev. Drug Discov.* 2004, 3, 499-508.
2. Guo, P. The Emerging Field Of RNA Nanotechnology. *Nat. Nanotechnol* 2010, 5, 833-842.
3. Guo, P.; Haque, F.; Hallahan, B.; Reif, R.; Li, H. Uniqueness, Advantages, Challenges, Solutions, And Perspectives In Therapeutics Applying RNA Nanotechnology. *Nucleic Acid Ther.* 2012, 22, 226-245.
4. Shu, Y.; Pi, F.; Sharma, A.; Rajabi, M.; Haque, F.; Shu, D.; Leggas, M.; Evers, B. M.; Guo, P. Stable RNA Nanoparticles As Potential New Generation Drugs For Cancer Therapy. *Adv. Drug Deliv. Rev.* 2014, 66, 74-89.
5. Guo, P.; Zhang, C.; Chen, C.; Garver, K.; Trottier, M. Inter-RNA Interaction Of Phage Phi29 Prna To Form A Hexameric Complex For Viral DNA Transportation. *Mol. Cell* 1998, 2, 149-155.
6. Shu, D.; Moll, W. D.; Deng, Z.; Mao, C.; Guo, P. Bottom-Up Assembly Of RNA Arrays And Superstructures As Potential Parts In Nanotechnology. *Nano Lett.* 2004, 4, 1717-1723.
7. Shu, Y.; Haque, F.; Shu, D.; Li, W.; Zhu, Z.; Kotb, M.; Lyubchenko, Y.; Guo, P. Fabrication Of 14 Different RNA Nanoparticles For Specific Tumor Targeting Without Accumulation In Normal Organs. *RNA* 2013, 19, 767-777.
8. Shu, D.; Khisamutdinov, E. F.; Zhang, L.; Guo, P. Programmable Folding Of Fusion RNA In Vivo And In Vitro Driven By PrNA 3WJ Motif Of Phi29 DNA Packaging Motor. *Nucleic Acids Res.* 2014, 42, E10.
9. Jasinski, D. L.; Khisamutdinov, E. F.; Lyubchenko, Y. L.; Guo, P. Physicochemically Tunable Polyfunctionalized RNA Square Architecture With Fluorogenic And Ribozymatic Properties. *ACS Nano* 2014, 8, 7620-7629.
10. Khisamutdinov, E. F.; Li, H.; Jasinski, D. L.; Chen, J.; Fu, J.; Guo, P. Enhancing Immunomodulation On Innate Immunity By Shape Transition Among RNA Triangle, Square And Pentagon Nanovehicles. *Nucleic Acids Res.* 2014, 42, 9996-10004.

11. Khisamutdinov, E. F.; Jasinski, D. L.; Guo, P. RNA As A Boiling-Resistant Anionic Polymer Material To Build Robust Structures With Defined Shape And Stoichiometry. *ACS Nano* 2014.
12. Shu, D.; Shu, Y.; Haque, F.; Abdelmawla, S.; Guo, P. Thermodynamically Stable RNA Three-Way Junction For Constructing Multifunctional Nanoparticles For Delivery Of Therapeutics. *Nat. Nanotechnol* 2011, 6, 658-667.
13. Haque, F.; Shu, D.; Shu, Y.; Shlyakhtenko, L. S.; Rychahou, P. G.; Evers, B. M.; Guo, P. Ultrastable Synergistic Tetravalent RNA Nanoparticles For Targeting To Cancers. *Nano Today* 2012, 7, 245-257.
14. Abdelmawla, S.; Guo, S.; Zhang, L.; Pulukuri, S. M.; Patankar, P.; Conley, P.; Trebley, J.; Guo, P.; Li, Q. X. Pharmacological Characterization Of Chemically Synthesized Monomeric Phi29 Prna Nanoparticles For Systemic Delivery. *Mol. Ther.* 2011, 19, 1312-1322.
15. Rush, D. Periconceptional Folate And Neural Tube Defect. *Am. J. Clin. Nutr.* 1994, 59, 511S-515S; Discussion 515S-516S.
16. Grapp, M.; Just, I. A.; Linnankivi, T.; Wolf, P.; Lucke, T.; Hausler, M.; Gartner, J.; Steinfeld, R. Molecular Characterization Of Folate Receptor 1 Mutations Delineates Cerebral Folate Transport Deficiency. *Brain* 2012, 135, 2022-2031.
17. Weitman, S. D.; Lark, R. H.; Coney, L. R.; Fort, D. W.; Frasca, V.; Zurawski, V. R., Jr; Kamen, B. A. Distribution Of The Folate Receptor GP38 In Normal And Malignant Cell Lines And Tissues. *Cancer Res.* 1992, 52, 3396-3401.
18. Steinfeld, R.; Grapp, M.; Kraetzner, R.; Dreha-Kulaczewski, S.; Helms, G.; Dechent, P.; Wevers, R.; Grosso, S.; Gartner, J. Folate Receptor Alpha Defect Causes Cerebral Folate Transport Deficiency: A Treatable Neurodegenerative Disorder Associated With Disturbed Myelin Metabolism. *Am. J. Hum. Genet.* 2009, 85, 354-363.
19. Parker, N.; Turk, M. J.; Westrick, E.; Lewis, J. D.; Low, P. S.; Leamon, C. P. Folate Receptor Expression In Carcinomas And Normal Tissues Determined By A Quantitative Radioligand Binding Assay. *Anal. Biochem.* 2005, 338, 284-293.
20. Low, P. S.; Henne, W. A.; Doorneweerd, D. D. Discovery And Development Of Folic-Acid-Based Receptor Targeting For Imaging And Therapy Of Cancer And Inflammatory Diseases. *Acc. Chem. Res.* 2008, 41, 120-129.
21. Croce, C. M. Causes And Consequences Of Microrna Dysregulation In Cancer. *Nat. Rev. Genet.* 2009, 10, 704-714.
22. Shu, Y.; Shu, D.; Haque, F.; Guo, P. Fabrication Of Prna Nanoparticles To Deliver Therapeutic Rnas And Bioactive Compounds Into Tumor Cells. *Nat. Protoc.* 2013, 8, 1635-1659.
23. Cheng, L.; Bao, S.; Rich, J. N. Potential Therapeutic Implications Of Cancer Stem Cells In Glioblastoma. *Biochem. Pharmacol.* 2010, 80, 654-665.
24. Mao, P.; Joshi, K.; Li, J.; Kim, S. H.; Li, P.; Santana-Santos, L.; Luthra, S.; Chandran, U. R.; Benos, P. V.; Smith, L.; et al. Mesenchymal Glioma Stem Cells Are Maintained By Activated Glycolytic Metabolism Involving Aldehyde Dehydrogenase 1A3. *Proc. Natl. Acad. Sci. U.S.A.* 2013, 110, 8644-8649.
25. Peruzzi, P.; Bronisz, A.; Nowicki, M. O.; Wang, Y.; Ogawa, D.; Price, R.; Nakano, I.; Kwon, C. H.; Hayes, J.; Lawler, S. E. et al. Microrna-128 Coordinately Targets Polycomb Repressor Complexes In Glioma Stem Cells. *Neuro Oncol.* 2013, 15, 1212-1224.
26. Li, J.; Zhu, S.; Kozono, D.; Ng, K.; Futalan, D.; Shen, Y.; Akers, J. C.; Steed, T.; Kushwaha, D.; Schlabach, M. et al. Genome-Wide Shrna Screen Revealed Integrated Mitogenic Signaling Between Dopamine Receptor D2 (DRD2) And Epidermal Growth Factor Receptor (EGFR) In Glioblastoma. *Oncotarget* 2014, 5, 882-893.
27. Martin-Villalba, A.; Okuducu, A. F.; Von Deimling, A. The Evolution Of Our Understanding On Glioma. *Brain Pathol.* 2008, 18, 455-463.
28. Leamon, C. P.; Parker, M. A.; Vlahov, I. R.; Xu, L. C.; Reddy, J. A.; Vetzel, M.; Douglas, N. Synthesis And Biological Evaluation Of EC20: A New Folate-Derived, (99m)Tc-Based Radiopharmaceutical. *Bioconjug. Chem.* 2002, 13, 1200-1210.
29. Ciafre, S. A.; Galardi, S.; Mangiola, A.; Ferracin, M.; Liu, C. G.; Sabatino, G.; Negrini, M.; Maira, G.; Croce, C. M.; Farace, M. G. Extensive Modulation Of A Set Of Micrornas In Primary Glioblastoma. *Biochem. Biophys. Res. Commun.* 2005, 334, 1351-1358.
30. Suh, S. S.; Yoo, J. Y.; Nuovo, G. J.; Jeon, Y. J.; Kim, S.; Lee, T. J.; Kim, T.; Bakacs, A.; Alder, H.; Kaur, B. et al. Micrornas/TP53 Feedback Circuitry In Glioblastoma Multiforme. *Proc. Natl. Acad. Sci. U.S.A.* 2012, 109, 5316-5321.
31. Quintavalle, C.; Garofalo, M.; Zanca, C.; Romano, G.; Iaboni, M.; Del Basso De Caro, M.; Martinez-Montero, J. C.; Incoronato, M.; Nuovo, G.; Croce, C. M. et al. Mir-221/222 Overexpression In Human Glioblastoma Increases Invasiveness By Targeting The Protein Phosphate Ptpmu. *Oncogene* 2012, 31, 858-868.
32. Quintavalle, C.; Donnarumma, E.; Iaboni, M.; Roscigno, G.; Garofalo, M.; Romano, G.; Fiore, D.; De Marinis, P.; Croce, C. M.; Condorelli, G. Effect Of Mir-21 And Mir-30b/C On TRAIL-Induced Apoptosis In Glioma Cells. *Oncogene* 2013, 32, 4001-4008.
33. Yoo, J. Y.; Pradarelli, J.; Haseley, A.; Wojton, J.; Kaka, A.; Bratasz, A.; Alvarez-Breckenridge, C. A.; Yu, J. G.; Powell, K.; Mazar, A. P. et al. Copper Chelation Enhances Antitumor Efficacy And Systemic Delivery Of Oncolytic HSV. *Clin. Cancer Res.* 2012, 18, 4931-4941.

What is claimed is:

1. A method of treating a brain tumor in a subject having or at risk of developing a brain tumor, the method comprising administering to the subject a therapeutically effective amount of a composition comprising an artificial RNA nanostructure molecule, wherein the molecule comprises a multiple branched RNA junction motif comprising at least one RNA oligonucleotide, and a brain tumor targeting module, wherein the module is coupled to an RNA junction motif, wherein the multiple branched RNA comprises a nucleotide sequence 5'-UUG CCA UGU GUA UGU GGG AUC CCG CGG CCA UGG CGG CCG GGA G-3' (SEQ ID NO: 6) or 5'-GATAAGCT CTC CCG GCC GCC ATG GCC GCG GGA T-3' (SEQ ID NO: 7).

2. A method of preventing brain tumor recurrence in a subject having or at risk of having brain tumor recurrence, the method comprising administering to the subject a therapeutically effective amount of a composition comprising an artificial RNA nanostructure molecule, wherein the molecule comprises a multiple branched RNA junction motif comprising at least one RNA oligonucleotide, and a brain tumor targeting module, wherein the module is coupled to an RNA junction motif wherein the multiple branched RNA comprises a nucleotide sequence 5'-UUG CCA UGU GUA UGU GGG AUC CCG CGG CCA UGG CGG CCG GGA G-3' (SEQ ID NO: 6) or 5'-GATAAGCT CTC CCG GCC GCC ATG GCC GCG GGA T-3' (SEQ ID NO: 7).

3. The method of claim 1, wherein the composition further comprises a pharmaceutically acceptable carrier.

4. The method of claim 1, wherein the subject is a mammal or a non-mammal vertebrate.

5. The method of claim 1, wherein the subject is a human.

6. The method of claim 1, wherein the brain tumor is glioblastoma.

7. The method of claim 1, wherein the molecule further comprises at least one bioactive agent coupled to the RNA junction motif.

8. The method of claim 1, wherein the RNA oligonucleotide comprises at least one chemical modification at the 2' position.

9. The method of claim 8, wherein the modification comprises 2' Fluoro, 2' Amine, 2' O-Methyl, or a combination thereof.

10. The method of claim 1, wherein the motif is a three-branched RNA junction motif.

11. The method of claim 1, wherein the diameter of the molecule is at least about 40 nm or less.

12. The method of claim 1, wherein the molecule has a zeta potential ranging from about −50 mV to about 50 mV.

13. The method of claim 10, wherein a branch of the three-branched RNA junction motif comprises an a3WJ RNA module (SEQ ID NO: 1); a b3WJ RNA module (SEQ ID NO: 2); a c3WJ RNA module (SEQ ID NO: 3); or a combination thereof.

14. The method of claim 1, wherein RNA oligonucleotides comprises at least 6 nucleotides in length.

15. The method of claim 1, wherein the brain tumor targeting module comprises a ligand that binds to at least one brain tumor cell surface marker.

16. The method of claim 15, wherein the ligand binds to a folate receptor, an EGFR, a transferrin receptor, an RGD, or a combination thereof.

17. The method of claim 15, wherein the ligand comprises an aptamer.

18. The method of claim 17, wherein the aptamer binds to EGFR, PDGFR, folate receptor, or a combination thereof.

19. The method of claim 1, wherein the targeting module comprises a folate.

20. The method of claim 7, wherein the bioactive agent comprises a drug, a therapeutic agent, a fluorescent dye, a chemical, an siRNA, an miRNA, an anti-miRNA, a ribozyme RNA, an antisense RNA or a combination thereof.

21. The method of claim 7, wherein the bioactive agent is directed to a brain tumor marker.

22. The method of claim 20, the microRNA sequence is at least 6 nucleotide in length.

23. The method of claim 20, wherein the bioactive agent is an anti-miRNA molecule for a miRNA comprising miR-9, miR-10b, miR-21, miR-17, or miR-26.

24. The method of claim 20, wherein the bioactive agent is a miRNA molecule for a miRNA comprising let-7a, miR-10b, miR-25, miR-34a, miR-124, miR-145, or miR-181b.

25. The method of claim 23, wherein the anti-miRNA comprises an anti-miRNA locked nucleic acid (LNA) molecule.

26. The method of claim 23, wherein the anti-miRNA LNA molecule comprises sequence 5'-GATAAGCT-3', 5'-AGCACTTT-3', or 5'-ATTTGCAC-3'.

27. The method of claim 20, wherein the siRNA binds to an mRNA molecule encodes a protein comprising VEGF, EGFR, POK, AKT, AGT, RAF, RAS, MAPK, ERK, MGMT, MMP-2, MMP-9, PDGF, PDGFR, IGF-1, HGF, mTOR, Cox-2 or TGFβ1.

28. The method of claim 20, wherein the siRNA binds to a mRNA molecule that encodes RAS, cMET, HER2, MDM2, PIK3CA, AKT, CDK4, or a combination thereof.

* * * * *